(12) United States Patent
Liscio et al.

(10) Patent No.: US 9,242,040 B2
(45) Date of Patent: Jan. 26, 2016

(54) SYRINGE ASSEMBLIES, METHODS OF FORMING SYRINGE ASSEMBLIES AND ADAPTERS FOR FORMING SYRINGE ASSEMBLIES

(75) Inventors: Edward P. Liscio, Murrysville, PA (US); Luis Castillo, Allison Park, PA (US); Michael McNeill, White Oak, PA (US); Mark W. Hitchins, Sewickley, PA (US)

(73) Assignee: Bayer HealthCare LLC, Whippany, NJ (US)

( * ) Notice: Subject to any disclaimer, the term of this patent is extended or adjusted under 35 U.S.C. 154(b) by 333 days.

(21) Appl. No.: 12/766,411

(22) Filed: Apr. 23, 2010

(65) Prior Publication Data

US 2011/0106015 A1 May 5, 2011

Related U.S. Application Data

(60) Provisional application No. 61/172,017, filed on Apr. 23, 2009.

(51) Int. Cl.
*A61M 5/145* (2006.01)

(52) U.S. Cl.
CPC ....... *A61M 5/14546* (2013.01); *Y10T 29/49826* (2015.01)

(58) Field of Classification Search
CPC .............. A61M 2005/14573; A61M 5/14216; A61M 5/1452; A61M 5/14546; A61M 5/1456; A61M 5/14566; A61M 5/1458
USPC .......... 604/131, 151, 152, 154, 155, 187, 218
See application file for complete search history.

(56) References Cited

U.S. PATENT DOCUMENTS

| | | |
|---|---|---|
| 4,006,736 A | 2/1977 | Kranys et al. |
| 4,082,094 A | 4/1978 | Dailey |
| 4,255,096 A | 3/1981 | Coker, Jr. et al. |
| 4,465,473 A | 8/1984 | Riiegg |
| 4,608,042 A | 8/1986 | Vanderveen et al. |
| 4,677,980 A | 7/1987 | Reilly et al. |
| 4,838,857 A | 6/1989 | Strowe et al. |
| 4,997,421 A | 3/1991 | Palsrok et al. |
| 5,383,851 A | 1/1995 | McKinnon, Jr. et al. |
| 5,383,858 A | 1/1995 | Reilly et al. |

(Continued)

FOREIGN PATENT DOCUMENTS

| | | |
|---|---|---|
| EP | 0584531 | 6/1999 |
| EP | 1016427 | 11/2004 |

(Continued)

OTHER PUBLICATIONS

US 3,694,139, 9/1972, Dedig et al. (withdrawn).

(Continued)

*Primary Examiner* — Kami A Bosworth
(74) *Attorney, Agent, or Firm* — David Schramm; Joseph L. Kent; James R. Stevenson

(57) ABSTRACT

Syringe assemblies and adapters for syringes that attach to and allow non-native syringes to be accepted by injectors having injector syringe interfaces adapted for particular types of syringes are described herein. Methods of forming the syringe assemblies, and kits including the syringe adapters which enable a non-native syringe to be operably attached to an injector are also described.

31 Claims, 14 Drawing Sheets

(56) References Cited

U.S. PATENT DOCUMENTS

| | | | |
|---|---|---|---|
| 5,520,653 | A | 5/1996 | Reilly et al. |
| 5,865,805 | A | 2/1999 | Ziemba |
| 5,873,861 | A | 2/1999 | Hitchins et al. |
| 5,899,885 | A | 5/1999 | Reilly et al. |
| 5,944,694 | A | 8/1999 | Hitchins et al. |
| 5,947,935 | A | 9/1999 | Rhinehart et al. |
| 5,951,063 | A * | 9/1999 | Szabo ................... F16L 37/144 285/303 |
| 5,964,483 | A * | 10/1999 | Long ..................... F16L 37/144 285/305 |
| 6,017,330 | A | 1/2000 | Hitchins et al. |
| 6,155,610 | A * | 12/2000 | Godeau ............... F16L 25/0045 285/242 |
| 6,312,410 | B1 | 11/2001 | Yamamoto |
| 6,322,535 | B1 | 11/2001 | Hitchins et al. |
| 6,336,913 | B1 | 1/2002 | Spohn et al. |
| 6,428,509 | B1 | 8/2002 | Fielder |
| 6,488,661 | B1 | 12/2002 | Spohn et al. |
| 6,569,127 | B1 | 5/2003 | Fago et al. |
| 6,585,700 | B1 | 7/2003 | Trocki et al. |
| 6,652,489 | B2 | 11/2003 | Trocki et al. |
| 6,676,634 | B1 | 1/2004 | Spohn et al. |
| 6,716,195 | B2 | 4/2004 | Nolan, Jr. et al. |
| 6,726,657 | B1 | 4/2004 | Dedig et al. |
| 6,743,205 | B2 | 6/2004 | Nolan, Jr. et al. |
| 6,821,013 | B2 | 11/2004 | Reilly et al. |
| 6,984,222 | B1 | 1/2006 | Hitchins et al. |
| 7,018,363 | B2 | 3/2006 | Cowan et al. |
| 7,019,458 | B2 | 3/2006 | Yoneda |
| 7,029,458 | B2 | 4/2006 | Spohn et al. |
| 7,273,477 | B2 | 9/2007 | Spohn et al. |
| 7,419,478 | B1 | 9/2008 | Reilly et al. |
| 7,462,166 | B2 | 12/2008 | Cowan et al. |
| 7,497,843 | B1 | 3/2009 | Castillo et al. |
| 7,691,085 | B2 | 4/2010 | Dedig et al. |
| 8,016,809 | B2 * | 9/2011 | Zinger et al. .................. 604/414 |
| 2001/0047153 | A1 | 11/2001 | Trocki et al. |
| 2002/0079696 | A1 * | 6/2002 | Szabo ............................. 285/39 |
| 2002/0177811 | A1 | 11/2002 | Reilly et al. |
| 2003/0045789 | A1 | 3/2003 | Thompson et al. |
| 2004/0064041 | A1 | 4/2004 | Lazzaro |
| 2004/0087909 | A1 | 5/2004 | Nemoto |
| 2005/0113754 | A1 | 5/2005 | Cowan |
| 2006/0264814 | A1 * | 11/2006 | Sage ............................... 604/67 |
| 2007/0250017 | A1 * | 10/2007 | Carred .............. A61M 5/31501 604/220 |
| 2008/0319421 | A1 * | 12/2008 | Bizup ................... A61M 39/12 604/535 |

FOREIGN PATENT DOCUMENTS

| | | |
|---|---|---|
| EP | 1351730 | 6/2006 |
| EP | 0919251 | 1/2007 |
| JP | 2005-504556 | 2/2005 |
| JP | 2005-506852 | 3/2005 |
| JP | 2009-536548 | 10/2009 |
| WO | 8900866 | 2/1989 |
| WO | 9221391 | 12/1992 |
| WO | 9707838 | 3/1997 |
| WO | 9707841 | 3/1997 |
| WO | 9736635 | 10/1997 |
| WO | 9910032 | 3/1999 |
| WO | 0108727 | 2/2001 |
| WO | 0137903 | 5/2001 |
| WO | 02056945 | 7/2002 |
| WO | 2004058332 | 7/2004 |
| WO | 2009073650 | 6/2009 |

OTHER PUBLICATIONS

International preliminary Examination Report for counterpart PCT Publication No. WO02/056947.

International Search Report for counterpart PCT Publication No. WO02/056947.

\* cited by examiner

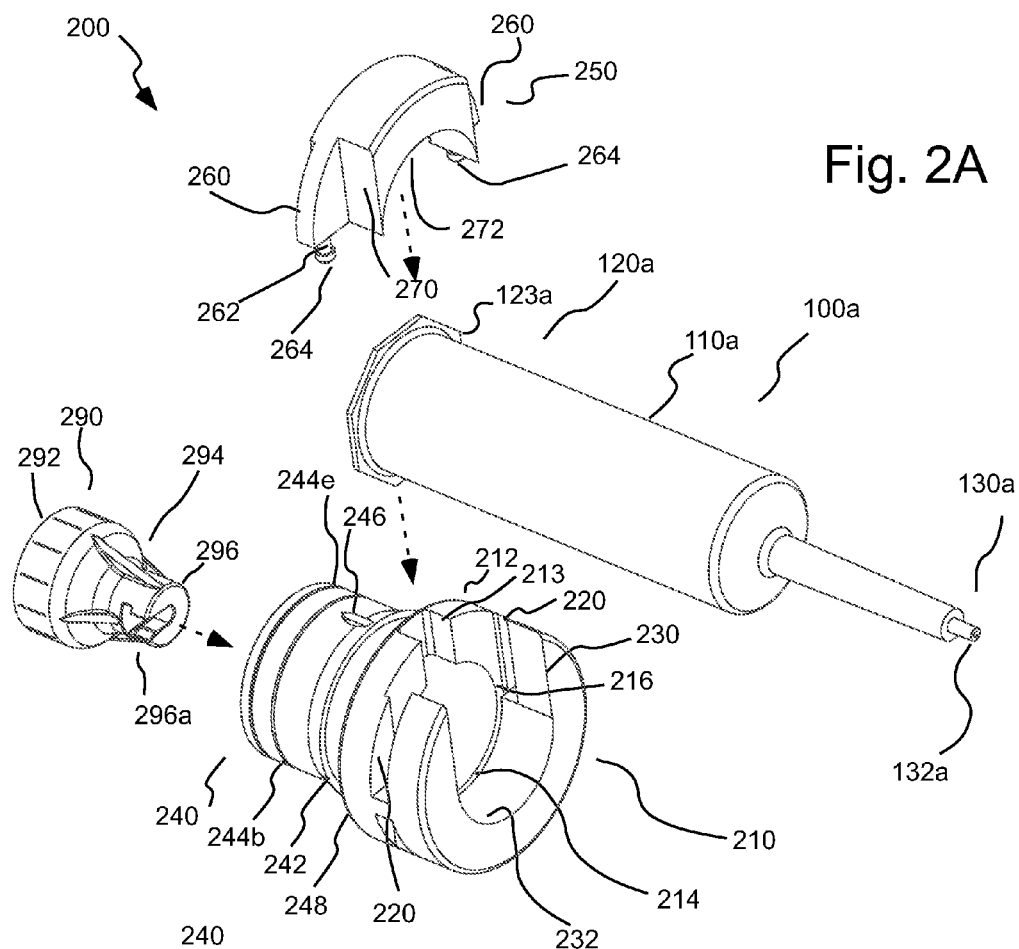
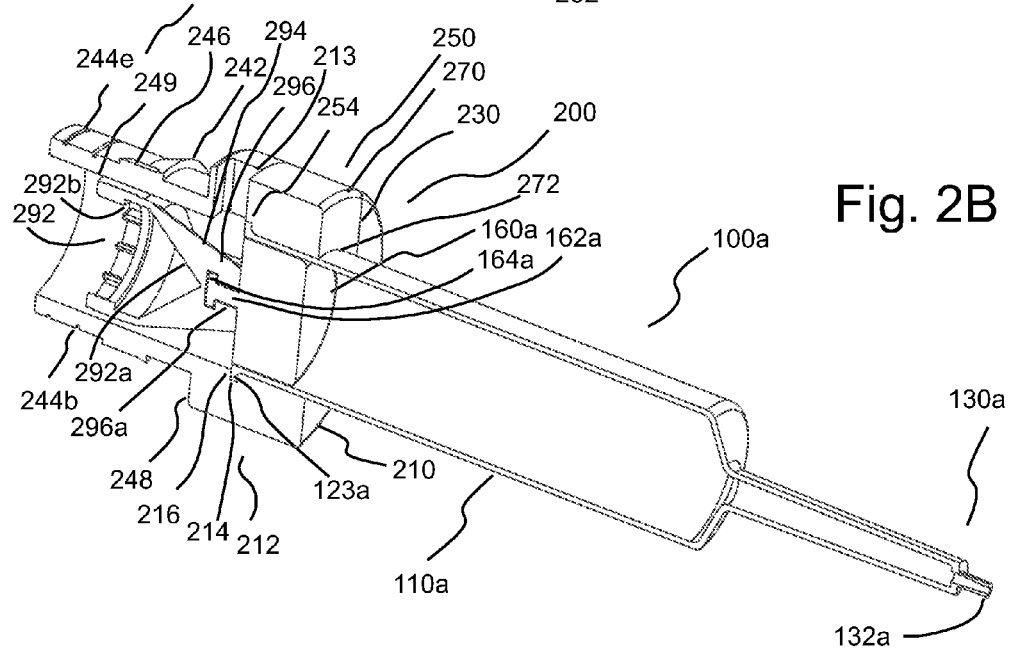

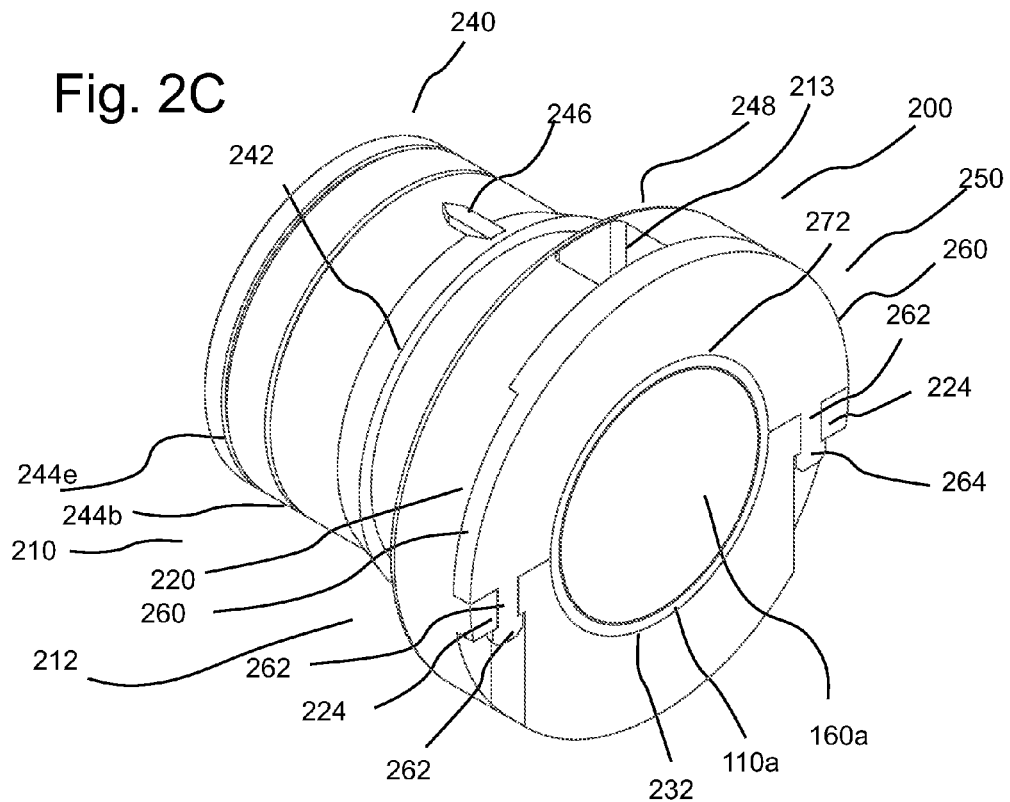
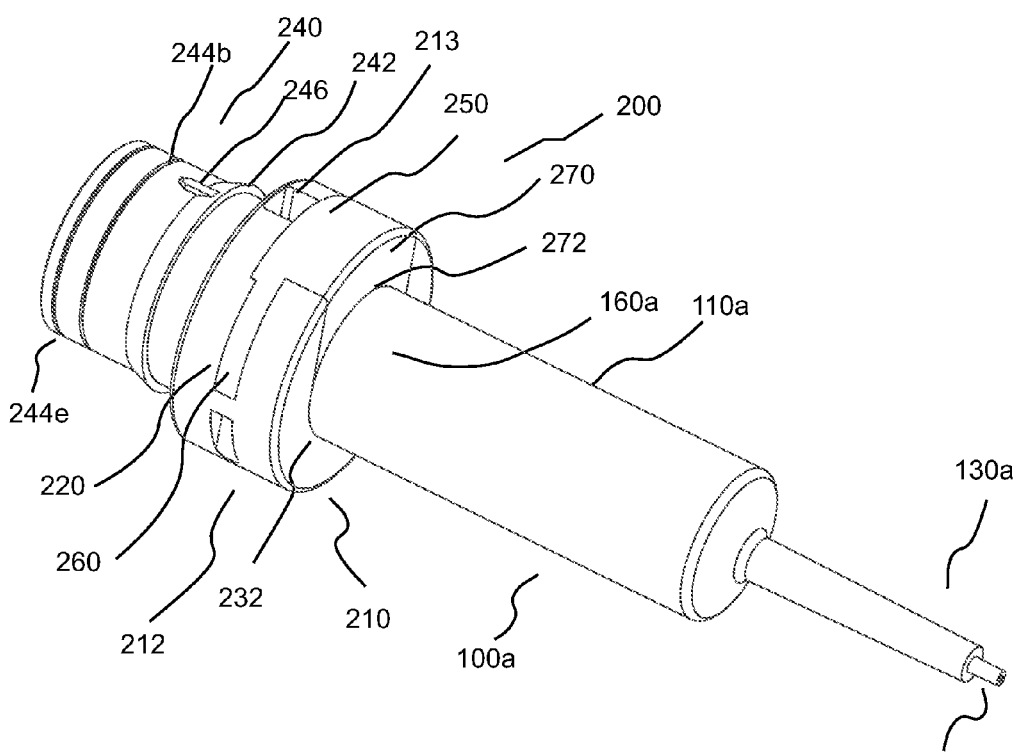

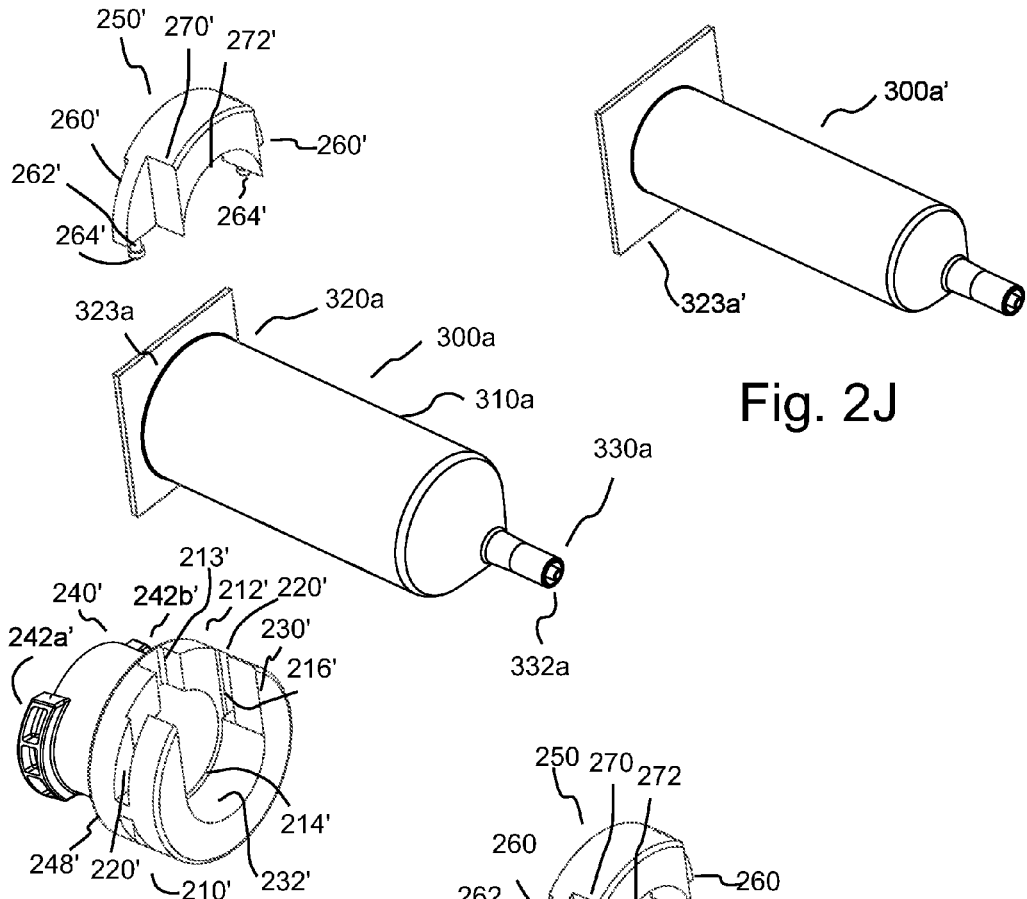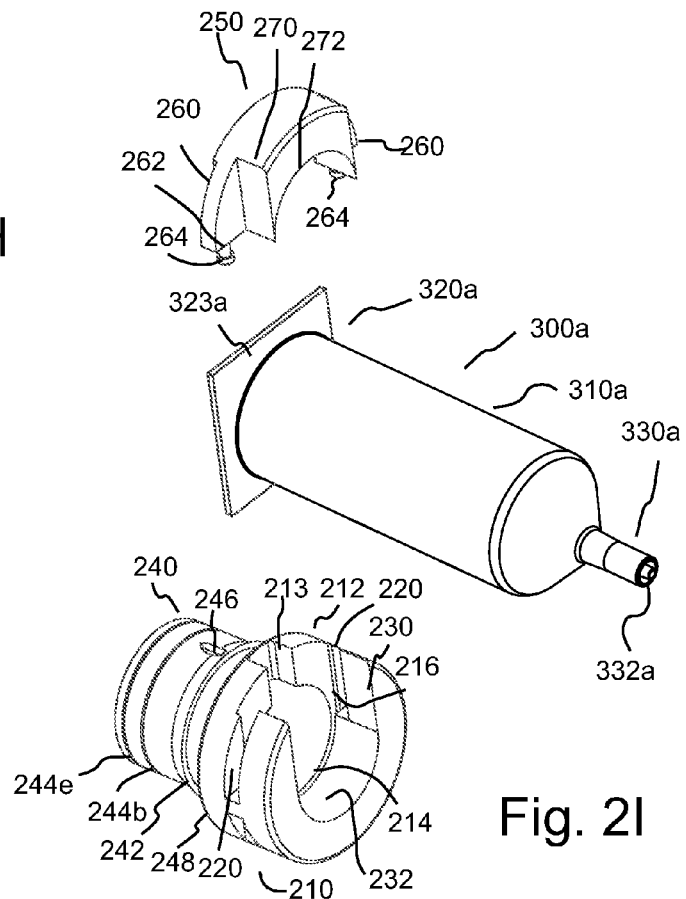

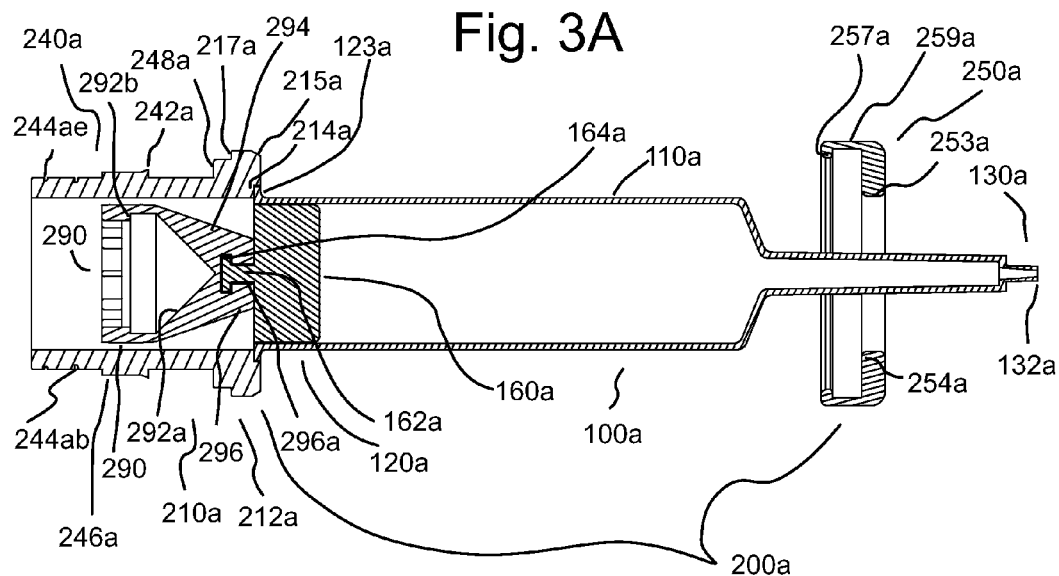
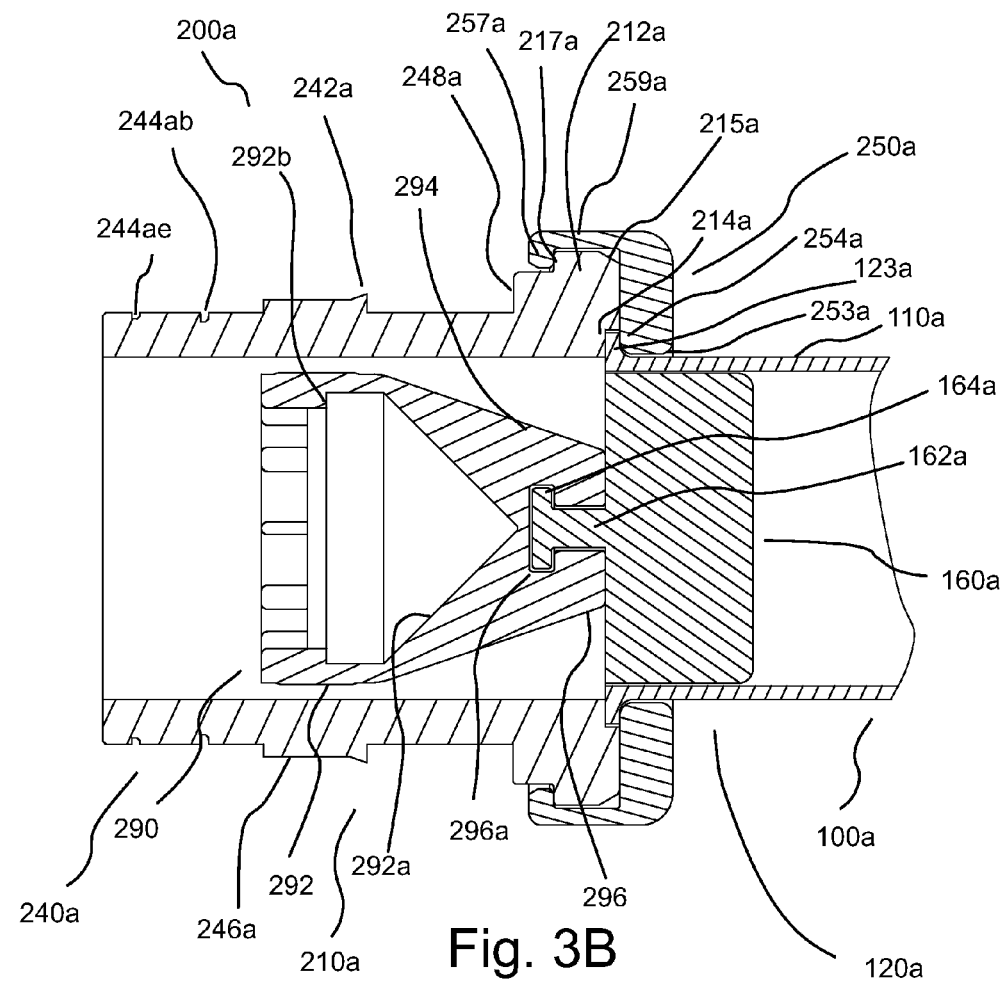

SYRINGE ASSEMBLIES, METHODS OF FORMING SYRINGE ASSEMBLIES AND ADAPTERS FOR FORMING SYRINGE ASSEMBLIES

CROSS REFERENCE TO RELATED APPLICATION

This application claims the benefit of U.S. Provisional Application Ser. No. 61/172,017, filed on Apr. 23, 2009, the contents of which are incorporated herein by reference.

BACKGROUND OF THE INVENTION

The present invention relates to syringe assemblies, to methods of forming syringe assemblies and to adapters for forming syringe assemblies.

The following information is provided to assist the reader to understand the invention disclosed below and the environment in which it will typically be used. The terms used herein are not intended to be limited to any particular narrow interpretation unless clearly stated otherwise in this document. References set forth herein may facilitate understanding of the present invention or the background of the present invention. The disclosure of all references cited herein are incorporated by reference.

Injector-actuated syringes and powered injectors are used in medical procedures including, but not limited to, therapeutic drug delivery and diagnostic drug delivery (for example, in angiography, computed tomography, ultrasound, NMR/MRI etc.). U.S. Pat. No. 4,006,736, for example, discloses an injector and syringe for injecting fluid into the vascular system of a human being or an animal. Typically, such injectors include a drive member such as a piston that connects to and imparts motion to a syringe plunger. For example, U.S. Pat. No. 4,677,980, the disclosure of which is incorporated herein by reference, discloses an angiographic injector and syringe wherein the drive member of the injector can be connected to, or disconnected from, the syringe plunger at any point along the travel path of the plunger via a releasable mechanism. A front-loading syringe and injector system is also disclosed in U.S. Pat. No. 5,383,858, the disclosure of which is incorporated herein by reference.

Various types of syringe interfaces are provided on injectors to place a syringe in operative connection with the injector. The front-loading injector of U.S. Pat. No. 5,383,858, for example, includes a bayonet syringe interface or mounting mechanism for securing the syringe to the front wall of the injector. In that regard, the syringe of U.S. Pat. No. 5,383,858 includes two generally opposed mounting flanges on a rearward end of the syringe which cooperate with corresponding retaining flanges on the injector thereof to form a bayonet connection.

U.S. Pat. No. 5,873,861 discloses another front-loading, bayonet-type syringe mounting mechanism in which multiple pairs or sets of syringe mounting flanges cooperate with corresponding pairs of injector retaining flanges to mount a syringe upon an injector. In one embodiment, a first pair of mounting flanges is offset from at least a second pair of mounting flanges. Other types of mounting mechanisms for front-loading syringes are disclosed in U.S. Pat. No. 6,652,489, the disclosure of which is incorporated herein by reference. In one embodiment of U.S. Pat. No. 6,652,489, a syringe includes a single engagement flange extending around the entire circumference of the syringe which removably engages a flex ring in the syringe interface of the injector to mount the syringe upon the injector.

In general, the use of specifically designed or unique mounting mechanisms or mounts on front-loading injectors prevents the use of syringes of various other types (that is, syringes having a mounting mechanism not directly compatible with the syringe interface/retaining mechanism of the front-loading injector or syringes without any such mounting mechanism) with the front-loading injectors. Furthermore, syringes designed for manual injection procedures are not directly connectible to injectors. Adapters attachable to front-loading injectors are sometimes used to allow the use of various types of syringes (including, for example, syringes designed for use with other injectors and/or syringes designed for manual injection) with front-loading injectors.

For example, U.S. Pat. No. 5,520,653 discloses several adapters designed to allow the use of various syringes with a front-loading injector. Another adapter for allowing use of various syringes with a front-loading injector is disclosed in Japanese Patent Publication No. 09-122234. Other adapters are disclosed, for example, in PCT Publication No. WO 01/08727 and U.S. Pat. Nos. 6,336,913, 6,488,661, 6,676, 634, 6,716,195, 6,726,657, 6,743,205, 7,0294,58, 7,273,477, and 7,497,843, the disclosures of which are incorporated herein by reference.

In general, such adapters include an injector interface to place the adapter in operative connection with the injector. The injector interface is typically designed to include a mounting mechanism similar to or the same as the mounting mechanism associated with syringes designed to be used in connection with the injector. The adapters also include a syringe interface to connect the syringe (which is not designed to be connected directly to the injector) to the adapter. A plunger adapter or plunger extension may also be provided to allow the injector piston to form an operative connection with the syringe. Currently available adapters are typically designed to connect to the injector to modify the syringe interface of the injector. Although such adapters are often referred to as "syringe adapters", they are more accurately defined to as "injector adapters" or "injector interface adapters." Once such an adapter is in place on the injector, any number of syringes can be used (serially) therewith.

Although a number of syringe interfaces and adapters are currently available, it remains desirable to develop improved syringe assemblies and syringe interfaces and adapters for use with syringes assemblies of various types.

SUMMARY OF THE INVENTION

In one aspect, a syringe assembly connectible to an injector including a syringe interface and a drive member is provided. The syringe assembly includes a syringe portion including a barrel section to contain fluid to be pressurized and an outlet in fluid connection with the barrel section. The syringe assembly also includes an adapter formed separately from the syringe portion and including a plurality of sections. At least two sections of the plurality of sections are engageable to nonremovably connect the adapter to the syringe portion. In a number of embodiments, the adapter includes only two sections to nonremovably connect the adapter to the syringe portion. The adapter further includes a mounting mechanism adapted to be connected to the injector syringe interface. The adapter can also include a passage in operative connection with the barrel section after connection of the adapter to the syringe portion so that upon connection of the adapter with the syringe portion, the drive member can pass through the passage to impart motion to a plunger slidably positionable within the barrel section.

The syringe portion can, for example, include a flange in the vicinity of a rearward section thereof. The at least two sections can be engageable so that the flange is nonremovably engaged by the adapter.

The at least two sections can, for example, be attachable via a mechanical connection. In several embodiments, the at least two sections are attachable via a snap fit. The snap fit can, for example, be a permanent snap fit.

The at least two sections can be brought together to be attached at a nonzero angle relative to a longitudinal axis of the barrel section. In a number of embodiments, the at least two section are brought together to be attached at an angle generally perpendicular to the longitudinal axis of the barrel section.

Each of the at least two sections is formed from a polymeric material. For example, each of the at least two sections can be formed separately from the other of the two sections via a molding process.

In several embodiments, the flange of the syringe portion is noncircular, and the at least two sections engage the flange so that the syringe portion cannot be rotated relative to the adapter.

One of at least two sections can, for example, include a rearward portion including the mounting mechanism and a forward portion to engage the other of the at least two sections.

In a number of embodiments, the adapter further includes at least a third section that is engageable with the at least two sections to assist in preventing disengagement of the connection (for example, a snap fit) between the at least two sections.

In another aspect, a method of forming a syringe assembly connectible to a first injector including a first syringe interface and a first drive member is provided, including: providing a syringe portion including a barrel section to contain fluid to be pressurized and an outlet in fluid connection with the barrel section; providing an adapter formed separately from the syringe portion and including a plurality of sections and a mounting mechanism adapted to be connected to the injector syringe interface; and forming an engagement between at least two sections of the plurality of sections to nonremovably connect the adapter to the syringe portion. The adapter can further include a passage in operative connection with the barrel section after engagement so that upon connection of the adapter with the syringe portion, the first drive member can pass through the passage to impart motion to a plunger slidably positionable within the barrel section. The syringe portion can, for example, include a mounting mechanism adapted to be connected to a second injector including a second syringe interface different from the first syringe interface of the first injector. The at least two sections can, for example, engage at least a portion of the mounting mechanism of the syringe portion to nonremovably connect the adapter to the syringe portion.

In a further aspect, a kit is provided to enable a syringe portion including a barrel section to contain fluid to be pressurized and an outlet in fluid connection with the barrel section to be operably connected to an injector including a syringe interface and a drive member. The kit includes an adapter including a plurality of sections. At least two sections of the plurality of sections are engageable to nonremovably connect the adapter to the syringe portion. The adapter further includes a mounting mechanism adapted to be connected to the injector syringe interface. The adapter can also include a passage in operative connection with the barrel section after connection of the adapter to the syringe portion so that upon connection of the adapter with the syringe portion, the drive member can pass through the passage to impart motion to a plunger slidably positionable within the barrel section.

In another aspect a method of forming a syringe assembly that is connectible to an injector including a syringe interface and a drive member is provided. The syringe assembly includes a syringe portion including a barrel section to contain fluid to be pressurized and an outlet in fluid connection with the barrel section. The method includes providing a kit including an adapter including a plurality of sections, at least two sections of the plurality of sections being engageable to nonremovably connect the adapter to the syringe portion, and a mounting mechanism adapted to be connected to the injector syringe interface. The adapter can further include a passage in operative connection with the barrel section after connection of the adapter to the syringe portion so that upon connection of the adapter with the syringe portion, the drive member can pass through the passage to impart motion to a plunger slidably positionable within the barrel section.

In still a further aspect, method of forming a plurality of syringe assemblies connectible to a plurality of injectors is provided. Each of the plurality of syringe assemblies includes a different unique mounting mechanism adapted to connect to a unique cooperating syringe interface on one of the plurality of injectors. The method includes: providing a plurality of syringe portions, each of the plurality of syringe portions including a barrel section to contain fluid to be pressurized and an outlet in fluid connection with the barrel section; providing a plurality of adapters formed separately from the plurality of syringe portions, each of the plurality of adapters including a plurality of sections and one of the unique mounting mechanisms; and forming an engagement between at least two sections of the plurality of sections of each of the plurality of injector interfaces to nonremovably connect each of the plurality of adapters to one of the plurality of syringe portions. At least two of the plurality of syringe portions can, for example, be generally identical (or the same in form and dimension).

The present invention, along with the attributes and attendant advantages thereof, will best be appreciated and understood in view of the following detailed description taken in conjunction with the accompanying drawings.

BRIEF DESCRIPTION OF THE DRAWINGS

FIG. 2A illustrates a side perspective view of an embodiment of a syringe adapter of the present invention in a disassembled or disconnected state and in position to be placed in operative connection with a syringe portion not designed to be directly connectable to the syringe interface of the injector.

FIG. 2B illustrates a perspective cutaway view of the syringe adapter of FIG. 2A in operative connection with the syringe portion.

FIG. 2C illustrates another perspective cutaway view of the syringe adapter of FIG. 2A in operative connection with the syringe portion.

FIG. 2D illustrates a perspective view of the syringe adapter of FIG. 2A in operative connection with the syringe portion.

FIG. 2H illustrates a perspective view of the use of a syringe adapter of the present invention in connection with a blank or generic syringe or syringe portion to manufacture a syringe assembly for use in connection with an injector.

FIG. 2I illustrates a perspective view of the use of another syringe adapter of the present invention in connection with a blank or generic syringe or syringe portion to manufacture a syringe assembly for use in connection with various injectors.

FIG. 2J illustrates a perspective view of another syringe portion of a substantially different volume than the syringes of FIGS. 2H and 2I for use in connection with one of the syringe adapters of FIG. 2H or 2I.

FIG. 3A illustrates a side perspective view of another embodiment of a syringe adapter of the present invention in a disassembled or disconnected state and in position to be placed in operative connection with a non-native syringe or syringe portion.

FIG. 3B illustrates a side, cross-sectional view of the syringe adapter of FIG. 3A in operative connection with the syringe portion.

DETAILED DESCRIPTION OF THE INVENTION

As used herein and in the appended claims, the singular forms "a," "an", and "the" include plural references unless the content clearly dictates otherwise. Thus, for example, reference to "a flange" includes a plurality of such flanges and equivalents thereof known to those skilled in the art, and so forth, and reference to "the flange" is a reference to one or more such flanges and equivalents thereof known to those skilled in the art, and so forth.

As described above, currently available adapters are designed to connect to an injector to "adapt" the syringe interface of the injector to enable the injector to be used in connection with a "non-native" syringe. As described above, the non-native syringe is not designed for use with the injector and does not include a mounting mechanism adapted to be used directly with the syringe interface of the injector. Once the adapter is placed in operative connection with the injector, a plurality of non-native syringes can typically be used (in series) with the adapter.

Unlike such adapters, the syringe adapters of the present invention can, for example, be attached to the non-native syringe or syringe portion prior to placing the adapter in operative connection with the injector. Further, the syringe adapters of the present invention can be designed so that any single adapter cannot be used with multiple syringes. Before discussing the adapters of the present invention, the operation of a representative injector 10 (in connection with which representative embodiments of the adapters of the present invention can be used) is discussed in operative connection with a representative native syringe 100.

One skilled in the art appreciates that the adapters of the present invention can be used in connection with virtually any injector and any non-native syringe or syringe portion simply by appropriate design of the injector interface mounting mechanism, injector interface section or injector interface portion of the adapter and appropriate design of the syringe interface portion of the adapter. In that regard, the syringe adapters of the present invention include a forward portion that includes a syringe interface to interact with and connect to the non-native syringe or syringe portion and a rearward portion that includes an injector interface to operatively connect the adapter to the syringe interface of the injector. The injector interface generally has a conformation similar to the mounting mechanism (for example, a flange configuration) found on native syringes (through which such native syringes are attached to the syringe interface of the injector).

Figure 1B:
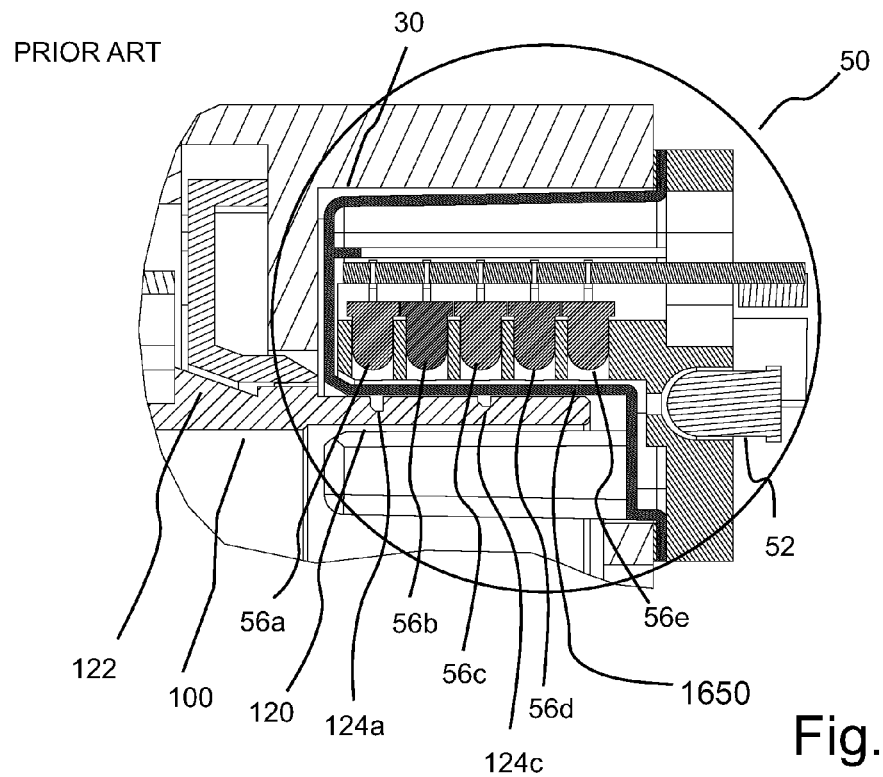
FIG. 1B illustrates an enlarged side cross-sectional view of a syringe sensing system of the syringe interface of FIG. 1A.
Figure 1A:
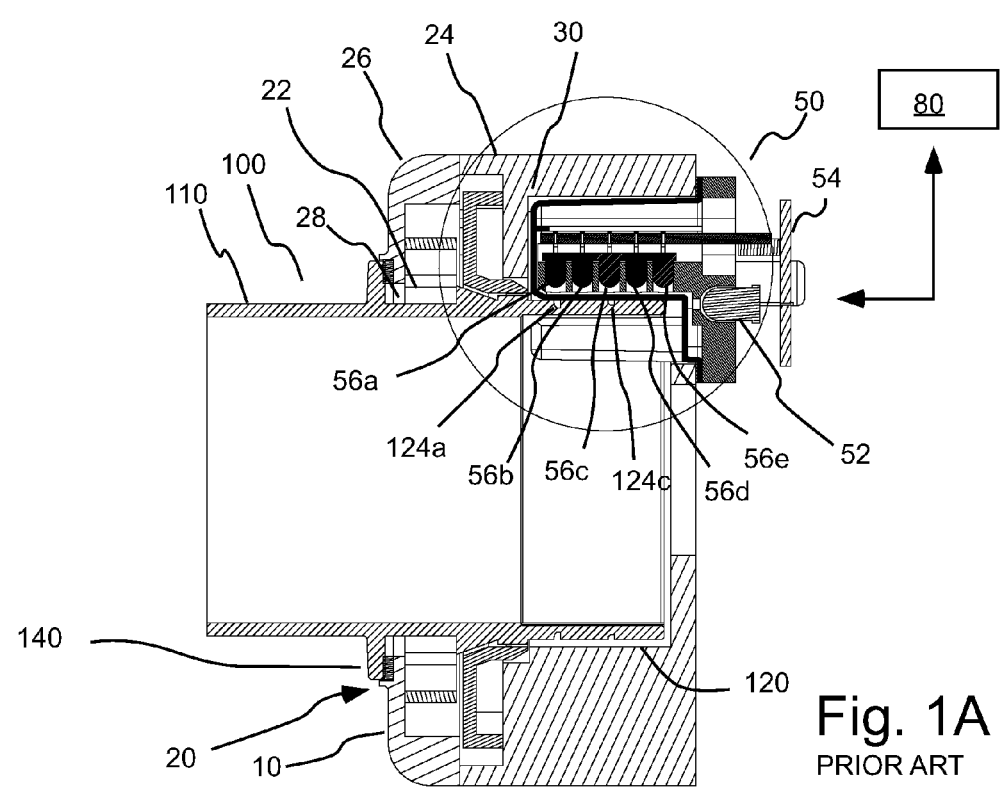
FIG. 1A illustrates a side cross-sectional view of a syringe interface of an injector with a syringe designed for use with the injector (sometimes referred to herein as a "native" syringe or, more generally, as a "syringe portion") in operative connection with the syringe interface.
Figure 1C:
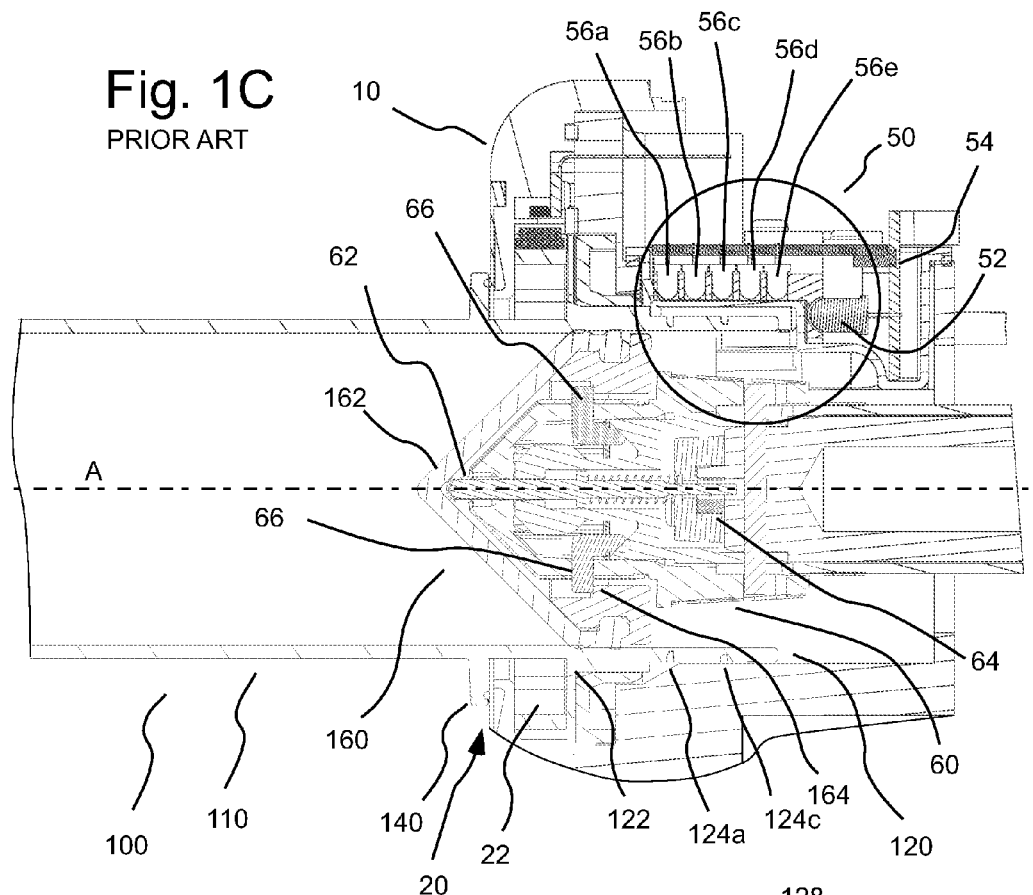
FIG. 1C illustrates another side cross-sectional view of the syringe interface of FIG. 1A illustrating the piston or drive member of the injector in operative connection with a plunger of a native syringe.
Figure 1D:
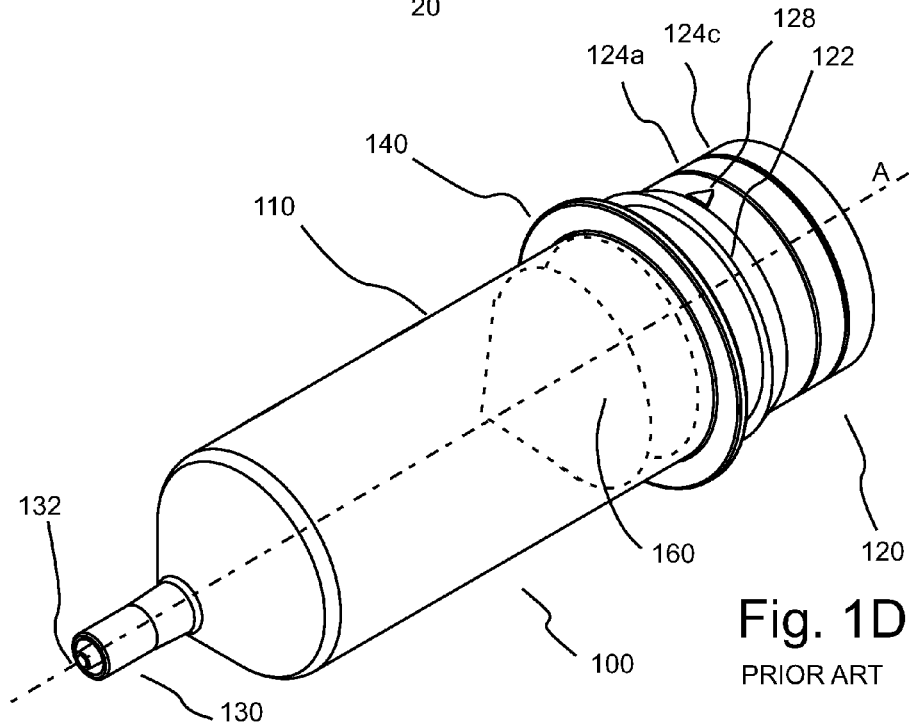
FIG. 1D illustrates a perspective view of a native syringe designed for use with the syringe interface of FIG. 1A.

FIGS. 1A through 1C illustrate a syringe interface 20 of injector 10 as described, for example, in U.S. Pat. Nos. 6,652,489 and 7,462,166 and found in commercial use in connection with the STELLANT™ injector, available from Medrad, Inc. of Indianola, Pa. USA. Referring, for example, to FIG. 1D, native syringe 100 includes a body or barrel portion 110 having a rear end 120 and a front end 130 including a fluid discharge or outlet 132. A tab, mounting member or mounting flange 122 is associated with barrel portion 110 adjacent to or at rear end 120 of syringe 100. In addition, a flange 140 (sometimes referred to as a drip flange) is preferably positioned forward of the mounting flange 122 to, for example, facilitate the engagement of syringe 100 to syringe interface 20 and/or to prevent fluid expelled from discharge or outlet 132 of syringe 100 from entering into injector 10 via syringe interface 20 (as, for example, described in U.S. Pat. No. 5,383,858).

As described in U.S. Pat. No. 6,652,489, syringe interface 20 comprises a flexible, retaining ring 22 disposed between a rear plate 24 and a front plate 26 which cooperates with mounting flange 122 of syringe 100. As rear end 120 of syringe 100 is passed through an opening 28 of syringe interface 20 and moved rearward, mounting flange 122 contacts ring 22 and causes flexing thereof. Mounting flange 122 includes a sloping section and a shoulder section that is essentially perpendicular to the exterior surface of cylindrical barrel portion 110. A rear ledge or surface of retaining ring 22 is adapted to engage a forward surface or shoulder of mounting flange 122 of syringe 100 when syringe 100 is fully installed in syringe interface 20. At least one, and preferably two or more, extending tabs or projections 128 are provided at rear end 120 of syringe 100. Upon rotation of syringe 100, tabs or projections 128 enable release of syringe 100 from engagement with syringe interface 20 as described in U.S. Pat. No. 6,652,489.

With reference to, for example, FIGS. 1A through 1D, as used herein to describe injector 10, syringe 100 and various embodiments of syringe adapters of the present invention, the terms "axial", "axially", "longitudinal, "longitudinally" and similar terms refer generally to, for example, an axis A (see FIGS. 1C and 1D) around which native syringe 100 and an injector derive member 60 can be formed (although not necessarily symmetrically therearound) and to directions collinear with or parallel to axis A. The terms "rear", "rearward" or similar terms refer generally to an axial or a longitudinal direction toward the end of injector 10 opposite the end to which syringe 100 (or an adapter of the present invention) is mounted. The terms "front", "forward" or similar terms refer generally to an axial or a longitudinal direction toward syringe discharge or outlet 132. The terms "radial", "radially" or similar terms refer generally to a direction normal to an axis such as axis A.

Injector 10 further includes a sensing assembly 50 in operative connection with syringe interface 20, the operation of which is described in U.S. Pat. No. 7,462,166. Sensor assembly 50 is positioned with a seating 30 of injector 10 in the vicinity of syringe interface 20. As described in U.S. Pat. No. 7,462,166, sensor assembly 50 includes a light emitter or light source 52 such as a light emitting diode. Light source 52 is in electrical connection with a printed circuit board 54, which controls operation of light source 52. Sensing assembly 50 also includes a plurality of sensors 56a-56e. Light from light source 52 travels or propagates in an axial direction through the light transmissive/translucent wall of syringe 100. Indicators such as indicators 124a and 124c are positioned at predetermined positions to reflect light to, for example, sensors 56a and 56c as described in U.S. Pat. No. 7,462,166 to provide information of the configuration of syringe 100 to control system 80 of injector 10. The positions of the indicators (and thereby the sensors to which the indicators reflect light) can, for example, correspond to a binary code associated with a syringe configuration.

As used herein, the term "syringe configuration" is used to encompass all information about a particular syringe (or syringe assembly as described herein), including, but not limited to, information about the mechanical properties of a syringe (for example, material, length and diameter) as well as information about the contents of the syringe (for example, volume and composition). With the advent of new syringes, and especially prefilled syringes, the need to accurately encode and sense (or read) syringe configuration variables is heightened. The syringe configuration information can be used by injector 10 to control the injection procedure as a function of defined syringe configuration/injection parameters. Moreover, a record of data associated with an injection procedure may be kept, for example, to satisfy accurate billing and cost information requirements under managed health care. A record may be maintained of information such as the type of syringe used, the amount of contrast medium used, the type of contrast medium used, the sterilization date, the expiration date, lot codes, the properties of the contrast media, and/or other clinically relevant information. Such information can be recorded digitally for sharing with computerized hospital billing systems, inventory systems, control systems, etc.

In FIG. 1C, a drive member or piston 60 of injector 10 is illustrated in operative connection with syringe plunger 160 of syringe 100. As described in Published U.S. Patent Application No. 2004/0064041, as piston 60 is advanced toward plunger 160 a biased (for example, spring-loaded) sensing pin 62 contacts the rearward or inward surface of a plunger cover 162. Pin 62 is forced rearward to so that it impinges upon the field of sensor 64 (for example, an optical sensor). Sensor 64 can signal control system 80 of injector 10 so that the control system stops advancement of piston 60 after a predetermined amount of time or distance of advancement of piston 60, so that piston 50 is brought into engagement with plunger 160, but advancement of piston 60 is stopped before movement of syringe plunger 160. Piston 60 can also include retractable pins 66 that form an abutting connection with one or more ledges, flanges or grooves 164 formed around the interior circumference of a plunger base 166 when piston 60 is to be retracted, thereby causing syringe plunger 160 to retract or move rearward along with piston 60. In FIG. 1C pins 66 on piston 60 are, for example, shown extended to form a connection with plunger 160 of syringe 100.

During advancement of piston 60 to engage plunger 160 as well as during advancement of piston 60 to advance plunger 160 within syringe 100 (for example, to expel air or fluid contained within syringe 100), pins 66 can be in a retracted state. If retraction of plunger 160 is desired, pins 66 can be extended to abut ledge 164.

FIGS. 2A through 2F illustrate an embodiment of a syringe adapter 200 operable to adapt a non-native syringe or syringe portion 100a for use in connection with syringe interface 20 of injector 10. Syringe adapter 200 is illustrated for use in connection with a representative example of a non-native syringe or syringe portion in the form of a 125 ml ULTRAJECT™ prefilled (that is, filled with injection fluid/contrast medium prior to being supplied to an end user) syringe 100a available from Covidien of Mansfield, Mass.

In the illustrated embodiment, syringe 100a includes a body or barrel portion 110a having a rear end 120a and a front end 130a including a fluid discharge or outlet 132a. An octagonal flange 123a extends radially outward from barrel portion 110 adjacent to or at rear end 120a of syringe 100a. A plunger 160a is slidably positioned within syringe barrel portion 110a. In the case of prefilled syringe 100a, plunger 160a is typically positioned near a rearward end of syringe barrel portion 110a.

Syringe adapter 200 cooperates with flange 123a to operatively connect syringe adapter 200 to non-native syringe 100a. In the embodiment illustrated in FIGS. 2A through 2D, syringe adapter 200 is formed in at least two sections. In that regard, a first section 210 and a second section 250 are interconnectable to engage, encompass or entrap flange 123a, thereby securely connecting syringe 100a to adapter 200.

First section 210 includes a forward portion 212 that interacts with syringe 100a (and second section 250) to connect syringe 100a thereto and a rearward or injector interface portion 240 to operatively connect adapter 200 to syringe interface 20. First section 210 includes a seating 214 that is dimensioned to receive and seat a portion of flange 123a upon lowering (in the orientation of the figures) of syringe flange 123a into seating 214. Abutment of flange 123a with a forward surface and a rearward surface of seating 214 prevents rearward and forward motion of syringe 100a relative to adapter 200. Second section 250 also includes a seating or surface 254 (see, for example, FIG. 2B) that abuts at least a portion of syringe flange 123a. The portion of syringe flange 123a abutted by surface 254 is positioned between rearward facing surface of seating 254 and a forward facing surface 216 of first section 210. Forward portion 212 of first section 210 can include a passage 213 to allow extending section 162a and flange 164a of plunger 160a to pass therethrough to form a cooperating connection with a plunger adapter 290 as discussed further below.

Second section 250 includes lateral extending sections 260 that are dimensioned to be slid within passages or slots 220 of first section 210. Downward (in the orientation of the figures) extending connectors or locking elements 262, which include enlarged end portions 264, form an interconnecting, locking or snap fit with passages, seatings or locating elements 224 of first section 210 as illustrated in FIG. 2C. In several embodiments, attempts to remove second section 250 from connection with second section 210 results in breakage of one or both of extending connectors 262 (and/or another portion of adapter 200) providing evidence of tampering and rendering adapter 200 unusable. In general, the connection between syringe adapter 200 and syringe portion 100a is non-removable in that syringe adapter 200 cannot be removed from connection with syringe portion 100a under forces experienced in normal storage, transportation use etc. Moreover, attempts to remove syringe adapter 200 from connection with syringe portion 100a can result in breakage as described above.

In general, a snap-fit is a mechanical joint system wherein a part-to-part attachment is accomplished with locating and locking features (sometimes referred to as constraint features) that are generally homogenous with one or the other of the components being joined. Forming a connection typically requires at least one flexible locking features to deflect or move for engagement with the mating part, followed by return of the locking feature toward its original position to accomplish the interference required to latch the components together. Locator features are a second, cooperating constraint feature, which are typically inflexible, and provide strength and stability in the attachment. Snap fits can be designed for making multiple, removable connections or for making a single, permanent connection (which typically cannot be disconnected without breakage).

Second section 250 also includes a forward extending central section 270 which is dimensioned to slide within a central slot 230 of first section 210. Upon complete connection of first section 210 and second section 250, an arced surface 232 of first section 210 and an arced surface 272 of second section 250 encompass the circumference of syringe barrel 110a.

Rearward or injector interface portion 240 of first section 210 includes elements that correspond to elements of rearward portion 120 of native syringe 100 to operatively connect syringe adapter 200 (and syringe 100a) to syringe interface 20. In that regard, mounting flange 242 corresponds to and operates in a similar manner to mounting flange 122. Indicators 244b and 244e correspond to and operate in a similar manner to indicators 124a and 124c of syringe 100 (and thereby cooperate with sensing system 60 to indicate the configuration of the adapter 200/syringe 100a assembly to injector control system 80). Further, projecting tab 246 corresponds to and operates in a similar manner to projecting tab 128 of syringe 100 to enable release of adapter 200 from operative connection with syringe interface 20. A radially extending ledge 248 at a rearward end of first portion 212 corresponds to and operates in a similar manner to flange 140 of syringe 100. Rearward or injector interface portion 240 further includes a generally central passage 249 therethrough to enable interaction of piston 60 with plunger 160a.

Figure 2E:
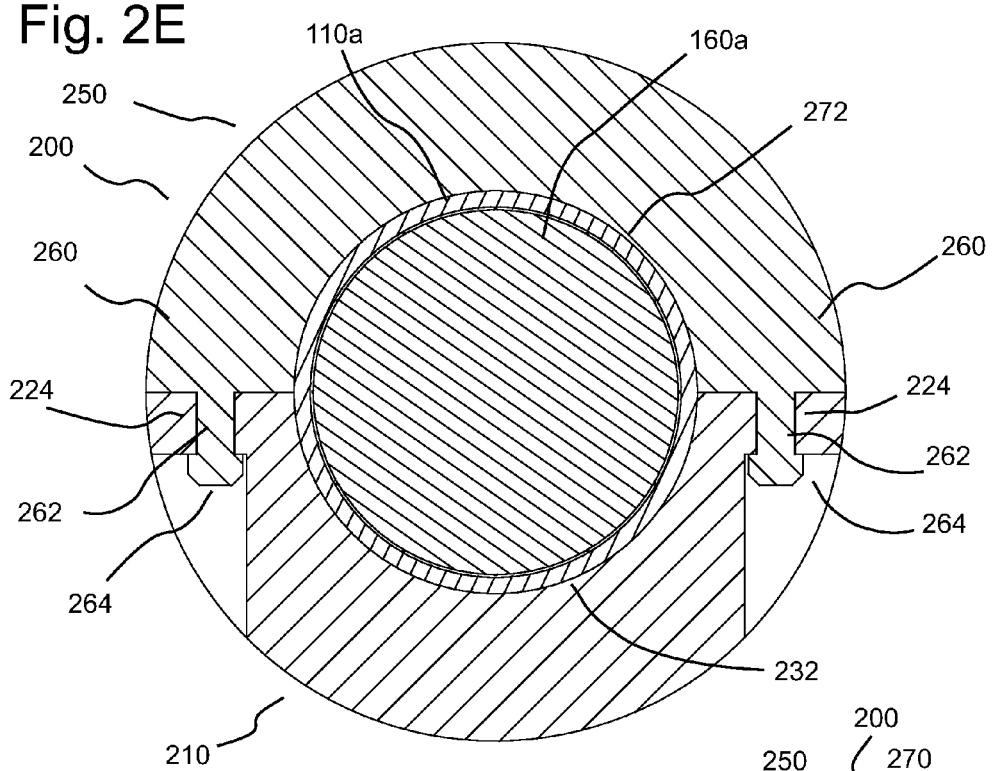
FIG. 2E illustrates an front cross-sectional view of the syringe adapter of FIG. 2A.
Figure 2F:
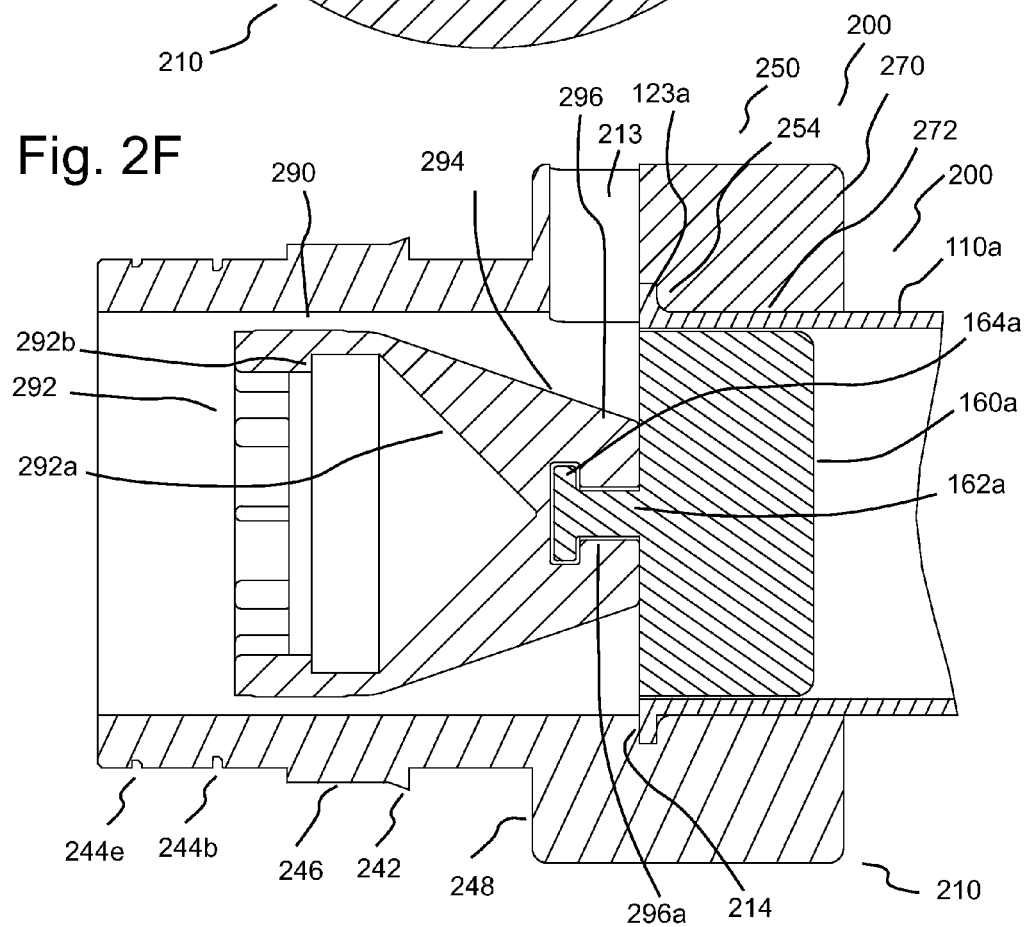
FIG. 2F illustrates a side cross-sectional view of the syringe adapter of FIG. 2A.

FIGS. 2A, 2B and 2F illustrate a representative embodiment of a plunger adapter 290 or plunger interface for use in connection with injector 10 and syringe 100a. Plunger adapter 290 includes a rear section 292 that can, for example, simulate or mimic the interaction of a rearward surface of plunger cover 162 of plunger 160 with piston 60 and sensing pin 62. Plunger adapter 290 can further include a forward extending section 294 and a forward, plunger contact section 296. Like other elements of plunger adapter 290, the length of extending section 294 can be adjusted for cooperating with individual syringe portion and/or syringe plunger characteristics.

In the case of a prefilled syringe such as a 25 ml ULTRA-JECT™ prefilled syringe 100a there may be no need to retract plunger 160a. Thus, there may be no need for piston 60 to capture or form an interlocking connection with rear section 292, and there may be no need for contact section 296 to capture or form an interlocking connection with plunger 160a. In that regard, if only forward motion is to be imparted to plunger 160a, rear section 292 can simply operate as a contact surface to form abutting contact with drive member 60, and contact section 296 can simply operate as a contact surface to form abutting contact with plunger 160a.

However, one skilled in the art appreciates, that rear section 292 can, for example, be formed similarly to plunger 160 to form an engagement with pins 66 of piston 60. In the illustrated embodiment, for example, rear section 292 of plunger adapter 290 includes a generally conical surface 292a that contacts a generally conical forward surface of drive member 60. Rear section 292 also includes a radially inward extending section or ledge 292b to form an abutting contact with pins 66 of drive member 60 to enable retraction of plunger adapter 290. Likewise, contact element 296 can include one or more capture elements or connectors to form a connection with plunger 160a such that rearward motion or retraction of piston 160a is enabled. In the illustrated embodiment, for example, plunger adapter 290 includes a seating 296a to form a cooperating connection with rear flange 164a on rearward extending member 162a of plunger 160a. In the case of a prefilled syringe, the syringe plunger is typically positioned far to the rear within the syringe barrel. In the illustrated embodiment, a connection can readily be made between seating 296a and rearward flange 164a during placement of syringe 100a in connection with syringe adapter 200.

Various other mechanism for forming an engagement between an injector drive member or piston and a syringe plunger (which can be used for manual or automated engagements between a drive member or piston and a plunger adapter as well as manual or automated engagements between a plunger adapter and a syringe plunger) are, for example, disclosed in U.S. Pat. No. 6,652,489 and U.S. Patent Application No. 2004/0064041, the disclosures of which are incorporated herein by reference.

A non-native syringe such as syringe 100a can be manufactured from various materials including, for example, one or more polymeric materials, glass, metal etc. A 25 ml ULTRAJECT™ prefilled syringe 100a is, for example, manufactured from polyethylene. In the embodiment described in connection with FIGS. 2A through 2E, first section 210 and second section 250 can, for example, be manufactured from resilient polymeric materials. In one embodiment, each of first section 210 and second section 250 are manufactured from polyethylene terephthalate (PET). PET provides the strength required for high pressure injection such as occurs in injection of CT contrast, while providing optical translucence required for operation of syringe adapter 200 in connection with light- or optical-based sensor assembly 50.

Use of polymeric materials for adapter 200 and other adapters of the present invention provides for simple and inexpensive manufacture (for example, via injection molding) and assembly (for example, via snap fits, welding, adhesives etc.) with a wide variety of non-native syringes or other syringe portions such as syringe 100a.

Use of a single adapter in connection with a single syringe can increase safety by decreasing the likelihood that the same syringe can be reused with different patients (thereby decreasing the associated risk of cross-contamination). Injector 10 can, for example, be programmed to not allow reuse of an adapter/syringe assembly previously used with injector 10 (as, for example, identified by sensor assembly 50). Adapters of the present invention can, for example, be provided to or manufactured by a syringe manufacturer as a kit to enable the syringe manufacturer to assemble adapter/syringe assemblies for use in connection with a wide variety of syringes and injectors. The relatively inexpensive adapter/syringe assemblies (or, simply, syringe assemblies) of the present invention can, for example, be disposed of after use. The adapters allow for a broader selection of pharmaceutical contrast medias to be used with a particular injector.

Figure 2G:
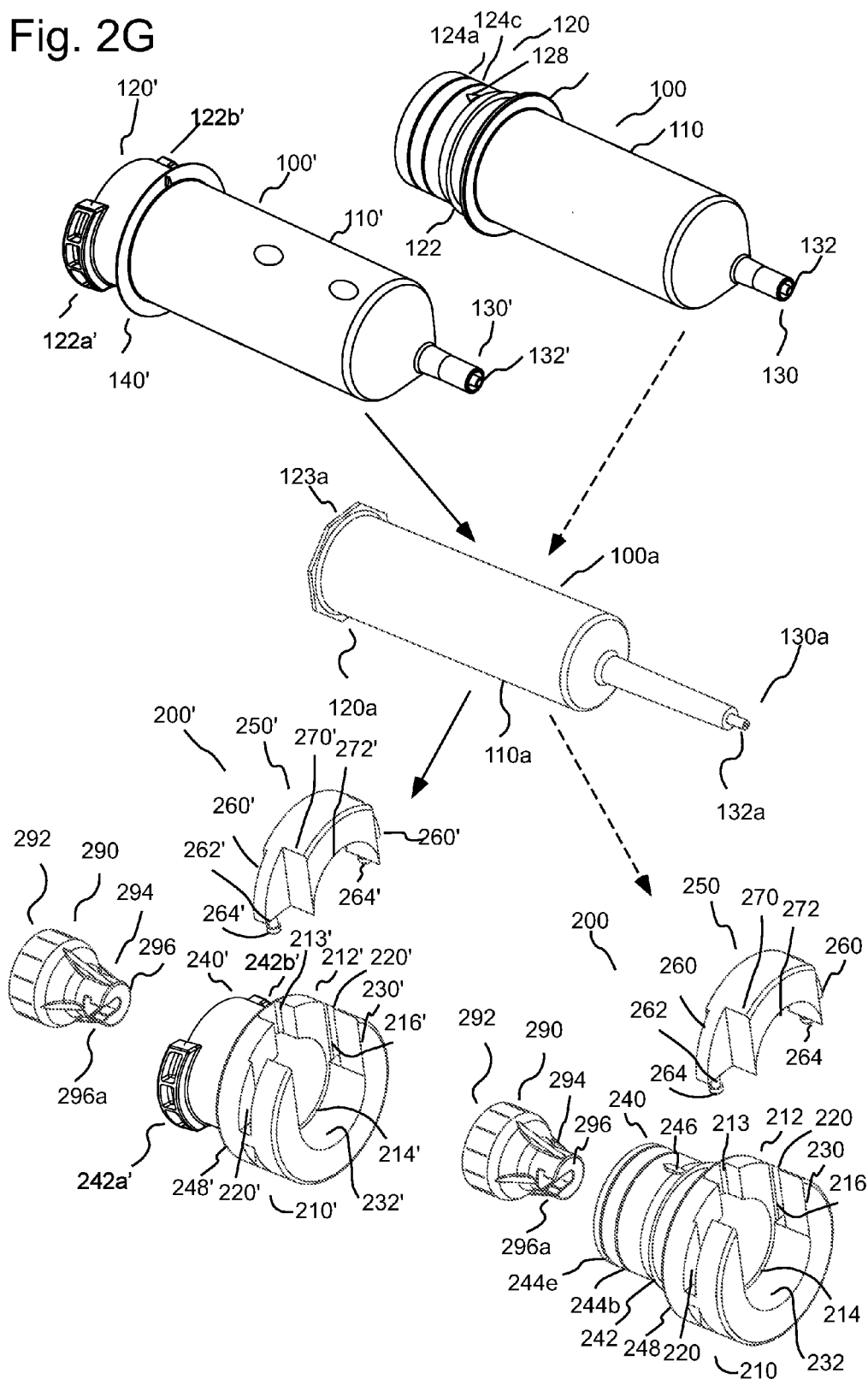
FIG. 2G illustrated a perspective view of syringe adapters similar in operation to the syringe adapter of FIG. 2A to adapt a syringe portion for use in connection with one of two different types of syringe interfaces of different injectors.

As clear to one skilled in the art, the adapters of the present invention are readily constructed to modify or adapt almost any syringe portion for use in connection with almost any front-loading injector. For example, FIG. 2G illustrates the adaptation or modification of syringe 100a for use in connection with either syringe interface 20 of injector 10 or a syringe interface of an injector as disclosed in, for example, U.S. Pat. No. 5,383,858. Syringe interfaces as disclosed in U.S. Pat. No. 5,383,858 are, for example, used in connection with the Medrad VISTRON™ CT injector, available from Medrad, Inc. Native syringe 100' includes a body or barrel portion 110' having a rear end 120' and a front end 130' including a fluid discharge or outlet 132'. Two mounting members or mounting flanges 122a' and 122b' are associated with barrel portion 110' adjacent to or at rear end 120' of syringe 100'. In addition, a flange 140 (sometimes referred to as a drip flange) is preferably positioned forward of the mounting flanges 122a' and 122b' to, for example, facilitate the engagement of syringe 100' to the syringe interface of the injector of U.S. Pat. No. 5,383,858 and/or to prevent fluid expelled from discharge or outlet 132' of syringe 100' from entering into the injector via the syringe interface.

Syringe adapter 200' cooperates with flange 123a of non-native syringe 100a to operatively connect syringe adapter 200' to non-native syringe 100a. In the embodiment illustrated in FIG. 2G, like syringe adapter 200, syringe adapter 200' is formed in at least two sections which are interconnectable to engage, encompass or entrap flange 123a. A forward portion 212' of first section 210' is identical in construction and operation to forward portion 212 of first section 210 of syringe adapter 200. Elements of forward portion 212' are numbered similarly to corresponding elements of forward portion 212 with the addition of the designation "'" thereto. Second section 250' is also identical in construction and operation to second section 250 of syringe adapter 200. Elements of second section 250' are numbered similarly to corresponding elements of second section 250 with the addition of the designation "'" thereto.

A rearward or injector interface portion 240' of first section 210' includes elements that correspond to elements of rearward portion 120' of native syringe 100' to operatively connect syringe adapter 200' (and syringe 100a) to the syringe interface of U.S. Pat. No. 5,383,858. In that regard, mounting flanges 242a' and 242b' correspond to and operate in a similar manner to mounting flanges 122a' and 122b'.

In addition to adapting non-native syringes, which can, for example, be commercially available syringes, for use in connection with various front-loading injectors, the syringe adapters of the present invention can be used in connection with a syringe blank or generic syringe to modify or adapt the syringe blank for use in connection with any one of various injector interfaces. The syringe blank need not correspond to, for example, a commercially available non-native syringe and need not be usable (without modification) in connection with any injector. As user herein, the terms "syringe" or "syringe portion" refer to a fluid container including a barrel section to contain fluid to be pressurized and an outlet in fluid connection with the barrel section. The terms include, for example, both non-native syringes and syringe blanks as described herein.

An example of a syringe blank 300a is illustrated in FIGS. 2H and 2I. Body or barrel portion 310a and a front end 330a (including fluid discharge or outlet 332a) of syringe blank 300a is generally identical to the corresponding elements of syringe 100' and/or syringe 100 illustrated in FIG. 2G. A syringe manufacturer which produces various syringes for use in connection with different injector interfaces can, for example, manufacture (or purchase from another manufacturer) a single syringe blank and adapt or modify that syringe blank to create a syringe assembly for use with any one of various injector interfaces as illustrated, for example, in FIGS. 2H and 2I, potentially simplifying manufacturing procedures and reducing manufacturing costs. In general, some modification of the seating 214' of syringe adapter 200' and seating 214 of syringe adapter 200 may be required for use in connection with syringe blank 300a (which has a square flange 323a as opposed to an octagonal flange). FIG. 2J illustrates a perspective view of another syringe portion 300a' of a substantially different volume and including a rearward flange 323a' for use in connection with one of the syringe adapters of the present invention as, for example, illustrated in FIG. 2H or 2I.

Once again, the sections of the syringe adapters of the present invention are readily formable from, for example, polymeric materials such as polyethyleneterephthalate (PET), polycarbonate and other polymeric materials via a molding process (for example, injection molding). Forming the syringe assemblies of the present invention can, for example, be less expensive than injection molding an integral or monolithic syringe including an injector mounting mechanism as often currently practiced.

Figure 2K:
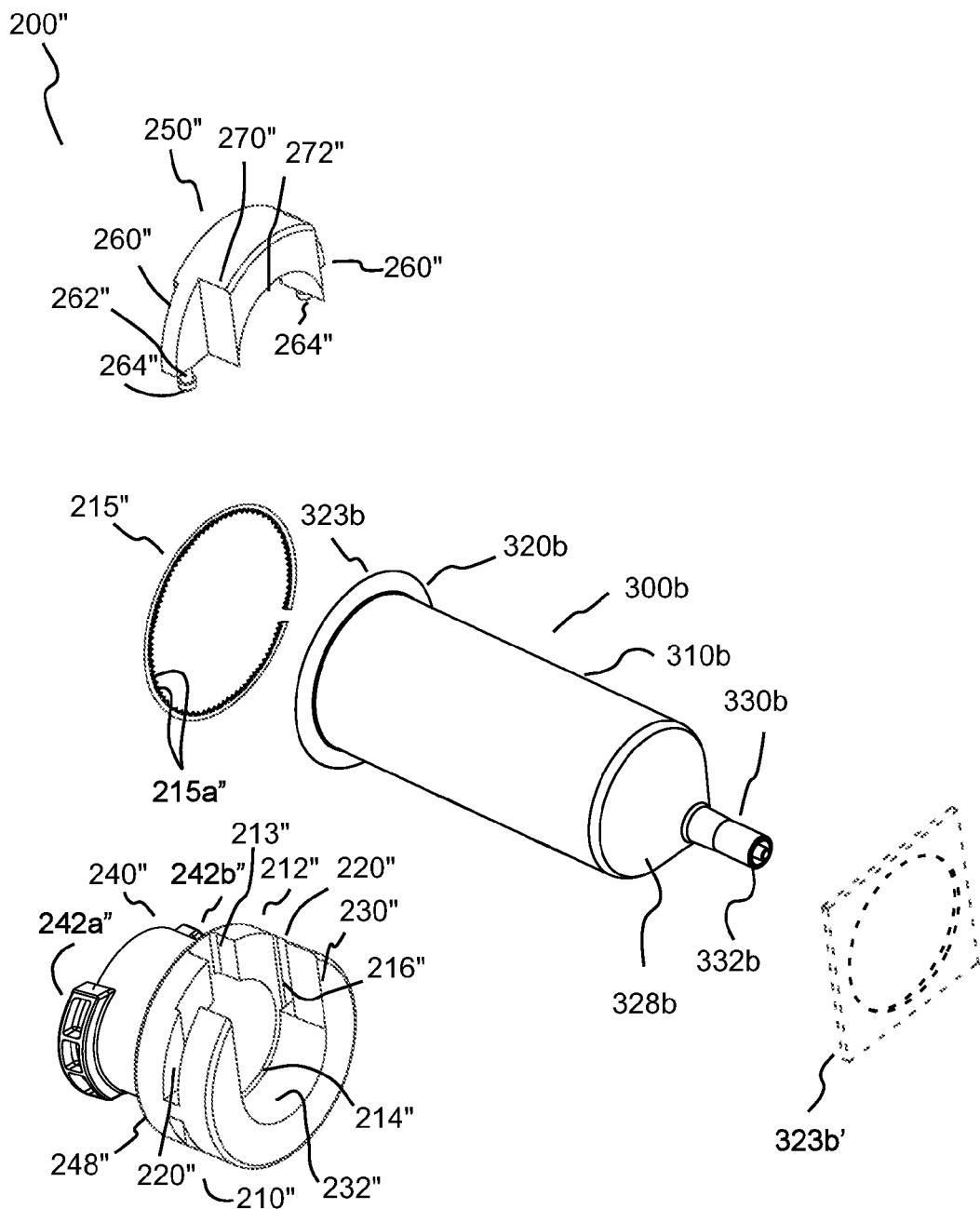
FIG. 2K illustrates the use of another syringe adapter of the present invention in connection with a blank or generic syringe or syringe portion with a generally circular rearward flange structure to manufacture a syringe assembly for use in connection with an injector.

In the cases of the syringe interfaces disclosed in each of U.S. Pat. Nos. 5,383,858, 5,873,861 and 6,652,489, for example, a user attaches and/or removes the syringe from connection with the corresponding syringe interface by grasping and rotating the syringe barrel of the integrally or monolithically formed syringe. For non-native syringe and syringe blanks including a rearward flange that is non-circular (for example, octagonal square, oval etc.), the cooperating seating of the syringe adapters of the present invention are readily sized and or dimensioned so that the syringe portion (for example, a non-native syringe or a syringe blank) cannot be rotated relative to the syringe adapter after the syringe adapter is connected to the syringe portion. Thus, a user can still grip the syringe barrel of the syringe portion of the syringe assembly and rotate the entire syringe assembly to attach the syringe assembly and/or remove the syringe assembly from connection with the syringe interface of the injector. In the case of a syringe portion 300b as illustrated in FIG. 2K including a circular rear flange 323b, it is somewhat more difficult to provide a seating 214" in a syringe adapter 200" to prevent rotation of non-native syringe or syringe blank 300b relative to syringe adapter 200". In cases of syringe interfaces as disclosed in U.S. Pat. Nos. 5,383,858, 5,873,861 and 6,652,489, wherein it is required to rotate the syringe mounting mechanism relative to the syringe interface to disconnect the syringe mounting mechanism therefrom, a user can simply grasp the syringe adapter of the present invention to rotate the syringe adapter to remove it from connection with the syringe interface. Grasping elements as known in the art (for example, knurled areas or extending flanges—not shown) can be provided on the syringe adapters of the present invention to facilitate grasping of the syringe adapter and rotation thereof relative to the syringe interface. Alternatively, a mechanism to, for example, engage syringe portion 300b can be incorporated in syringe adapter 200" to prevent rotation of syringe portion 300b relative to syringe adapter 200". In the embodiment illustrated in FIG. 2J, for example, syringe adapter 200" includes a flexible ring 215" including gripping or grasping members such as teeth 215a". Upon connection of adapter 200" with syringe portion 300b, teeth 215a" of flexible ring 215" are forced against the perimeter of flange 323b by first section 210" and second section 250" to prevent rotation of syringe portion 300b relative to syringe adapter 200". In other respects, syringe adapter 200" operates in a similar manner to syringe adapter 200' and elements of syringe adapter 200" are referenced similarly to corresponding elements of syringe adapter 200' with the replacement of the designation "'" with the designation "''".

A non-circular member 323b' as illustrated in FIG. 2K in dashed lines can, for example, be used to assist in forming a connection between a syringe adapter of the present invention and a syringe portion having a rearward flange that differs in, for example, size and/or shape, from the seating of the syringe adapter. In the embodiment of FIG. 2K, member 323b' can cooperate with flex ring 215" to engage syringe portion 300b and prevent rotation of syringe portion 300b relative to syringe adapter 200".

The syringe adapters of the present invention need not cooperate with a rearward flange of a syringe portion as discussed in connection with the above-described embodiments. The syringe adapters of the present invention can, for example, cooperate with any portion of the syringe over which a change in radius occurs. For example, the syringe adapters of the present invention can form a cooperating abutting connection with a forward transition region 328b of syringe portion 300b (see, for example, FIGS. 3G and 3H and the discussion thereof below).

FIGS. 3A and 3B illustrate another embodiment of a syringe adapter 200a for use with 25 ml ULTRAJECT™ prefilled syringe 100a. In a number of respects, syringe adapter 200a operates in a similar manner to syringe adapter 200 and several elements of syringe adapter 200a are referenced similarly to corresponding elements of syringe adapter 200 with the addition of the designation "a" thereto.

Like syringe adapter 200, syringe adapter 200a cooperates with flange 123a to form an operative connection with syringe 100a. In the embodiment illustrated in FIGS. 3A and 3B, syringe adapter 200a is formed in at least two sections, a first section 210a and a second section 250a, which are interconnectable to engage, encompass or entrap flange 123a. First section 210a includes a forward portion 212a that interacts with syringe 100a to connect syringe 100a thereto and a rearward or injector interface portion 240a to operatively connect adapter 200a to syringe interface 20. Rearward portion or injector interface 240a is generally identical in construction and operation to rearward or injector interface portion 240 and operates in a manner similar to rear end 120 of native syringe 100 to connect adapter 200a to syringe interface 20 of injector 10. In that regard, mounting flange 242a corresponds to and operates in a similar manner to mounting flange 122. Indicators 244ab and 244ae correspond to and operate in a similar manner to indicators 124a and 124c of syringe 100, and cooperate with sensing assembly 50 to identify and/or indicate the configuration of the adapter 200a/syringe 100a assembly to injector control system 80. Further, projecting tab 246a corresponds to and operates in a similar manner to projecting tab 128 of syringe 100 to enable release of adapter 200a from operative connection with syringe interface 20. A radially outward extending ledge 248a at a rearward end of first portion 212a corresponds to and operates in a similar manner to flange 140 of syringe 100.

First section 210 includes a generally octagonal seating 214a formed in first portion 212 thereof which is dimensioned to receive octagonal flange 123a. A rearward surface of flange 123a abuts a forward facing surface of seating 214a. Second section 250a also includes a rearward facing surface 254 (see, for example, FIG. 2B) which abuts a forward facing surface of syringe flange 123a. Syringe flange 123a is thereby positioned between rearward facing surface 254 and a forward facing surface of seating 214.

Second section 250 includes a generally circular passage 253a which is dimensioned to have a diameter slightly larger than the outer diameter of syringe barrel 110a. During assembly, syringe flange 123a is seating in seating 214a and second section 250a is placed over syringe 100a and moved rearward (with syringe barrel 110a passing through opening 253a). A radially inward extending flange or locking element 257a on a rearward extending section 259a of second section 250a is caused to deflect outward upon contact with first section 210a and form a snap fit with a ledge 217a of first section 210a as, for example, illustrated in FIG. 3B. First portion 212a can, for example, includes a bevel 215a on a forward surface thereof to facilitate radially outward deflection of flange 257a and extending section 259a. Once a secure engagement is formed between first section 210a and second section 250a, a rearward surface of seating 254a of second section 250a abuts syringe flange 123a as described above, preventing forward movement of syringe 100a relative to adapter 200a. Syringe flange 123a is thereby captured or entrapped between first section 210a and second section 250a.

The 90° angle (with respect to the syringe portion longitudinal axis) of the forward surface of flange 257a results in a permanent snap fit. Thus, attempts to remove second section 250a from connection with first section 210a will result in breakage of flange 257a, extending section 259a or another portion of first section 210a or second section 250a to provide evidence of tampering and to render adapter 200a unusable. One or more portions of adapter 200a can, for example, be designed to fail upon such tampering or attempt to remove syringe 100a.

Figure 3C:
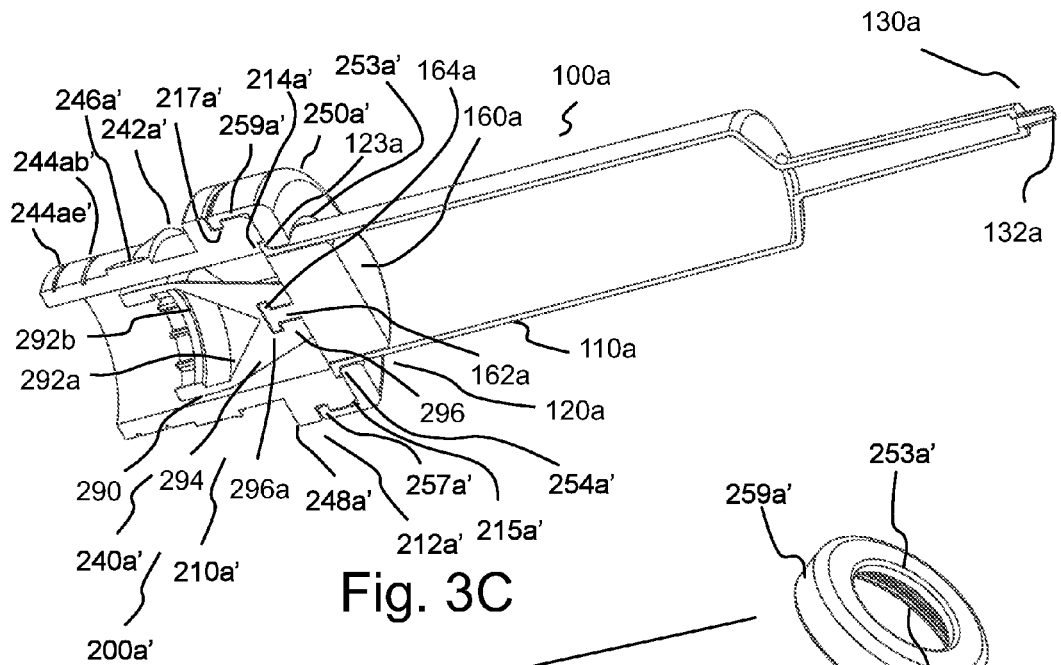
FIG. 3C illustrates a perspective cutaway view of a syringe adapter similar in operation to the syringe adapter of FIG. 3A in operative connection with the syringe portion.
Figure 3D:
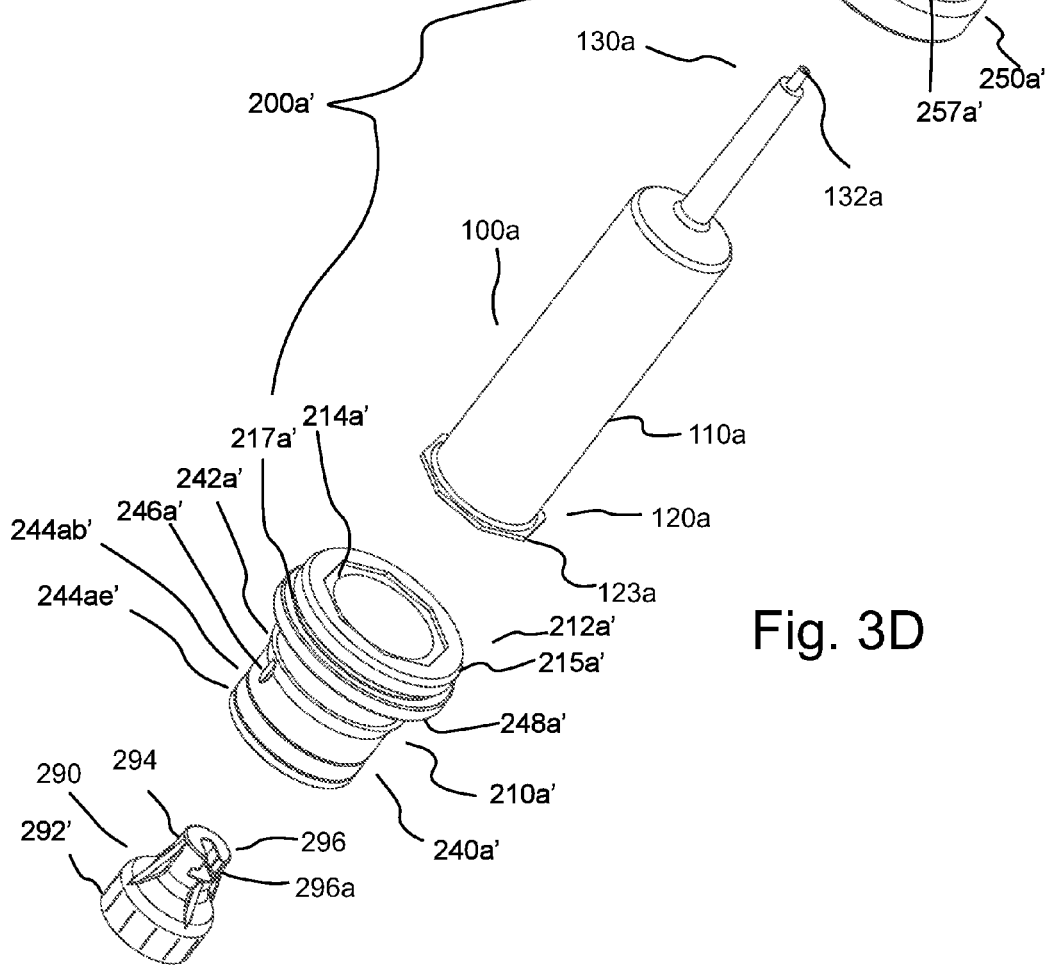
FIG. 3D illustrates a perspective view of the syringe adapter of FIG. 3C in a disassembled or disconnected state and in alignment to be operatively connected to a syringe portion.
Figure 3E:
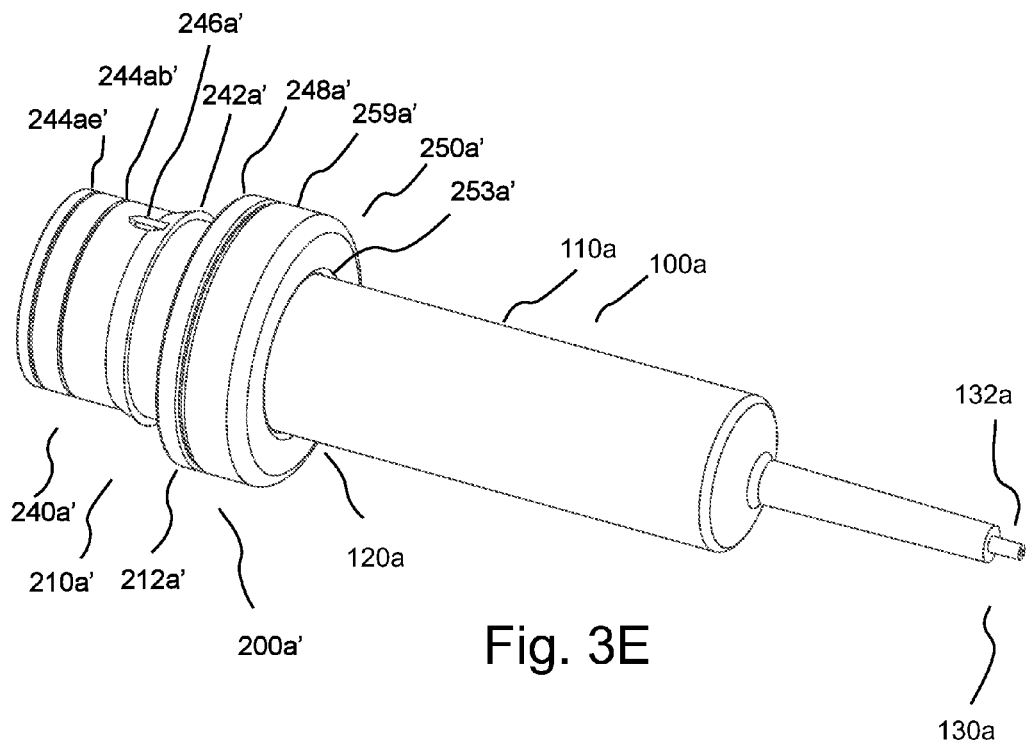
FIG. 3E illustrates a perspective view of the syringe adapter of FIG. 3C in operative connection with the syringe portion.

FIGS. 3C through 3E illustrate another embodiment of a syringe adapter 200a' that is similar in design to syringe adapter 200a. In general, the only difference between syringe adapter 200a' and syringe adapter 200a is that first section 210a' forms a cooperative connection with flange 257a' of second section 250a' via a seating or radially inward projecting annular depression or groove 217a' rather than via ledge 217a of first section 210a. Groove 217a makes it more difficult to access flange 257a' in any attempt to disconnect second section 250a' from first section 210a'. In other respects, syringe adapter 200a' operates in a similar manner to syringe adapter 200a and elements of syringe adapter 200a' are referenced similarly to corresponding elements of syringe adapter 200a with the addition of the designation "'" thereto.

Figure 3F:
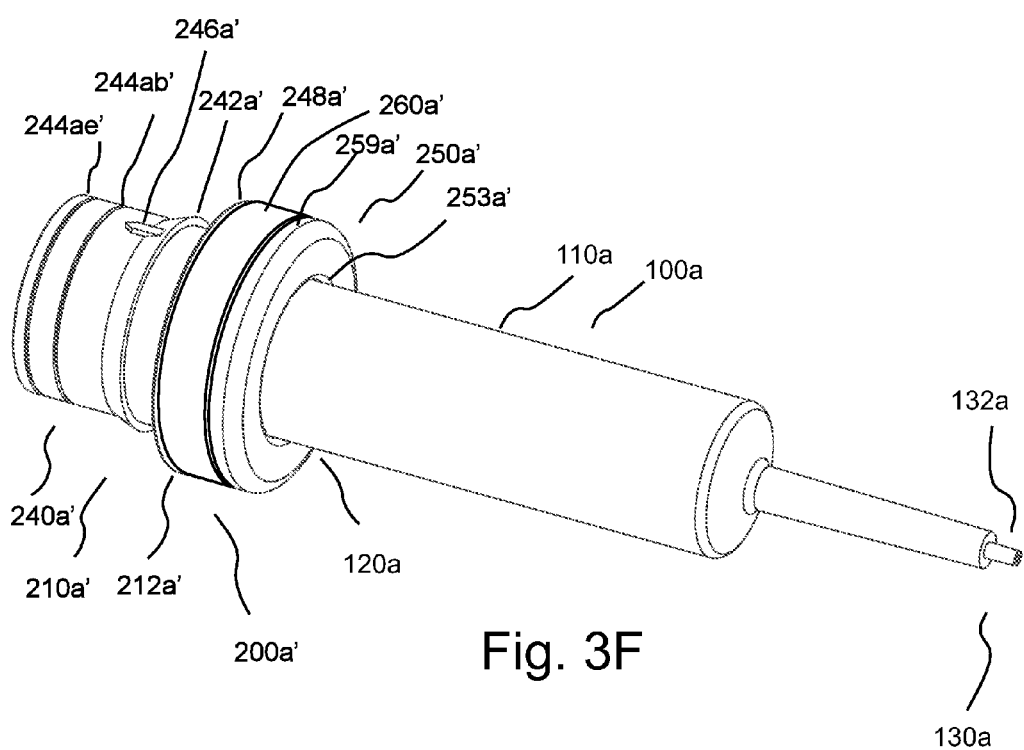
FIG. 3F illustrates a perspective view of the syringe adapter of FIG. 3C in operative connection with the syringe, wherein another section has been engaged with the syringe adapter to assist in maintaining the syringe adapter in engagement with the syringe portion.

FIG. 3F illustrates the use of a third section 260a', which is generally cylindrical or annular in shape, to encompass at least a portion of forward portion 212a' and extending section 259a'. Third section 260a' helps to ensure that the snap fit between first section 210a' and second section 250a' remains permanent by, for example, further limiting access to the snap fit elements and by preventing radially outward deflection of extending section 259a' before, during or after use. Third section 260a' can, for example, be a strip of a fiber reinforced tape or a flexible, open annular member including a closure mechanism (for example, a permanent snap fit closure).

Figure 3G:
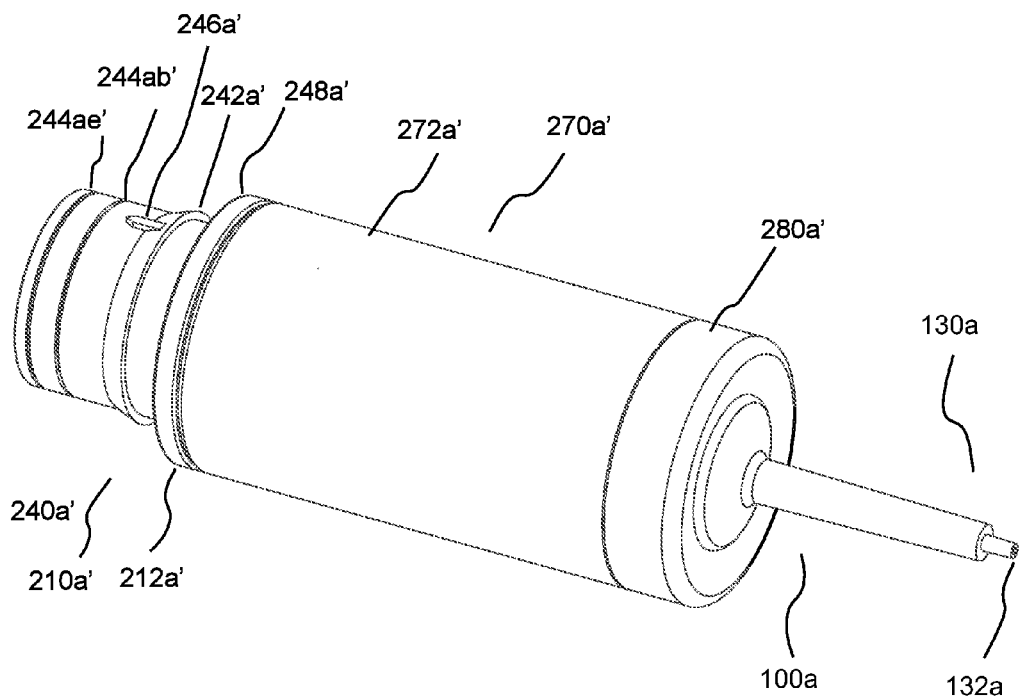
FIG. 3G illustrates a perspective view of another embodiment of a syringe adapter of the present invention, which operates in a manner similar to the syringe adapter of FIG. 3C, but which includes a pressure jacket.

In injection procedures such as angiographic injection procedures, pressures within syringe barrels are relatively high (for example, up to approximately 1500 psi). Such high injection pressures can cause certain polymeric syringe barrel walls to bulge or to expand, resulting in a phenomena referred to a "capacitance" or "stored energy" in the system. In extreme cases, the syringe can burst or fail as a result of the high pressures. As known in the art, pressure jackets can be used to at least partially encompass a syringe barrel to provide support therefor (see, for example, PCT International Publication No. WO 2004/058332). FIGS. 3F and 3G illustrate the use of a pressure jacket assembly 270a' with first section 210a'. In the illustrated embodiment, pressure jacket assembly 270a' includes a first generally cylindrical member 270a' dimensioned to have an inner diameter slightly larger than the outer diameter of syringe barrel 110a and adapted to provide support to syringe barrel 110a. First member 270a' includes a cantilevered, inward extending flange or locking element 274a' to form a permanent snap fit with groove 217a'. Pressure jacket assembly 270a' also includes a forward, second generally cylindrical or generally annular member or cap 280', which includes a cantilevered, inward extending flange or locking element 282a' to form a permanent snap fit with groove 276a' of first cylindrical member 272a'.

Figure 3H:
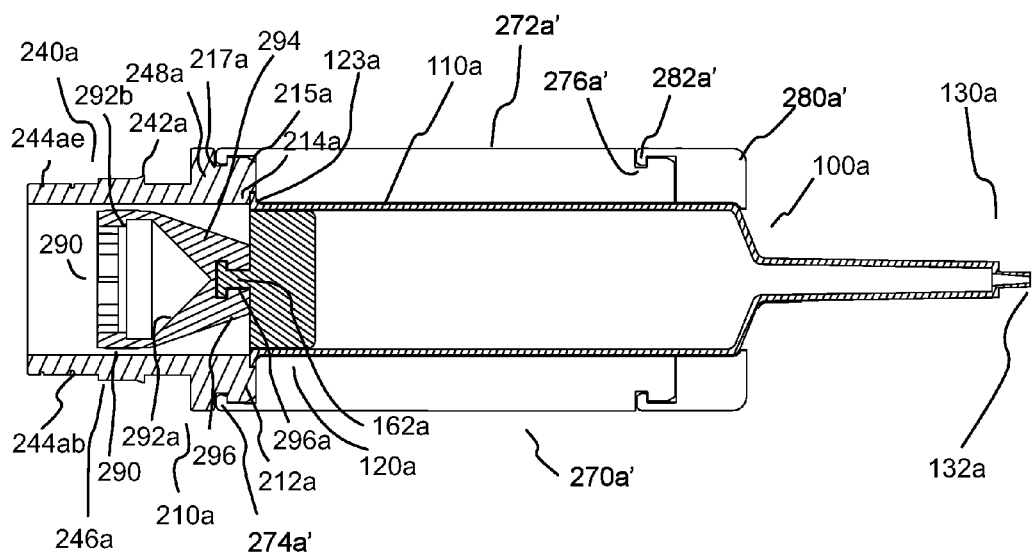
FIG. 3H illustrates a cross-section view of the syringe adapter of FIG. 3F.

FIGS. 3G and 3H also illustrate one manner in which an engagement can be made with a forward section of syringe portion over which a radius of the syringe portion changes. Such an engagement can, for example, be made in a syringe portion not including a rearward flange (such as flange 123a) to connect and adapter to the syringe portion.

Figure 4A:
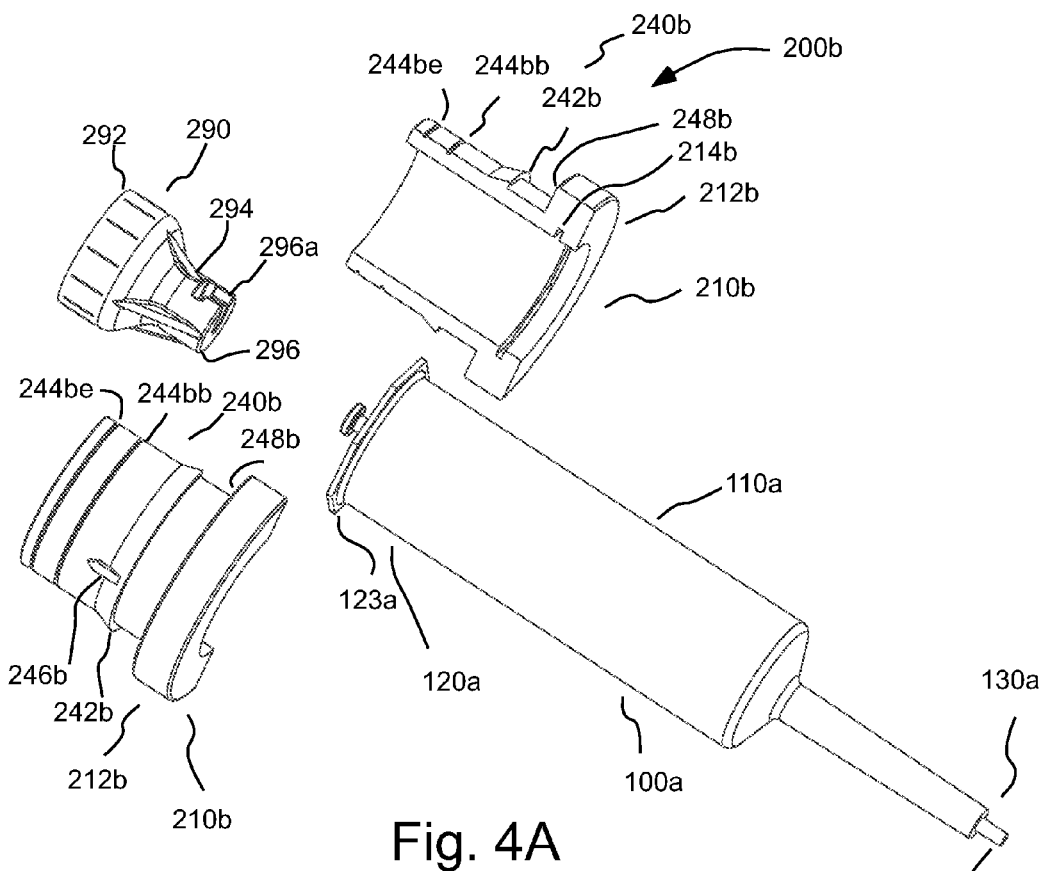
FIG. 4A illustrates a side perspective view of another embodiment of a syringe adapter of the present invention in a disassembled or disconnected state and in position to be placed in operative connection with a non-native syringe or syringe portion.
Figure 4B:
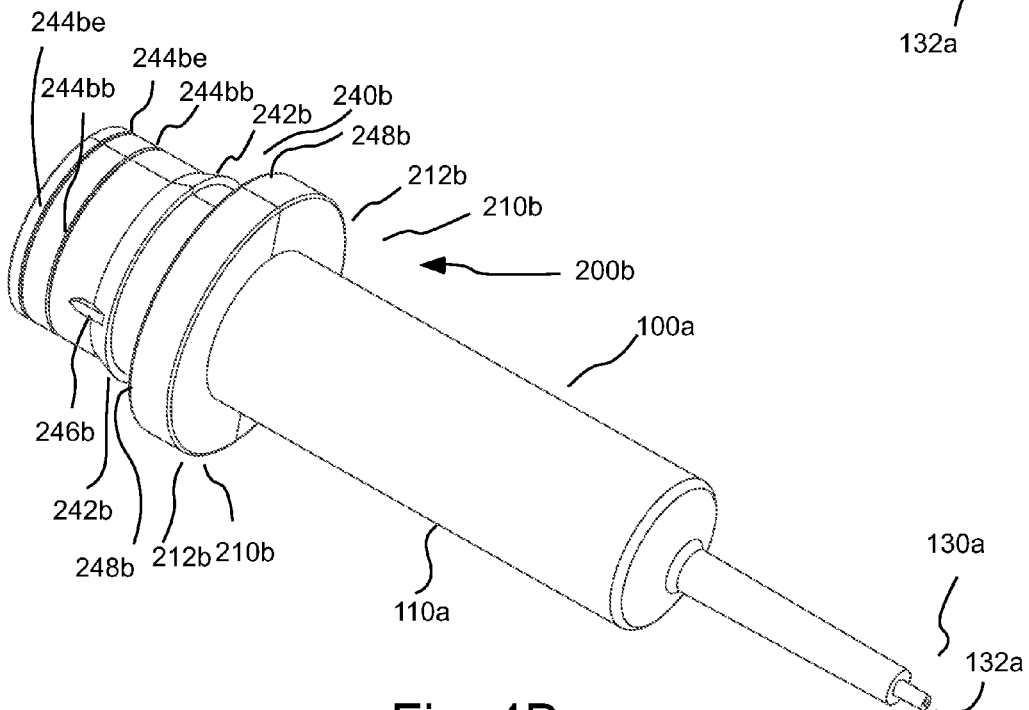
FIG. 4B illustrates a perspective view of the syringe adapter of FIG. 4A in operative connection with the syringe portion.
Figure 4C:
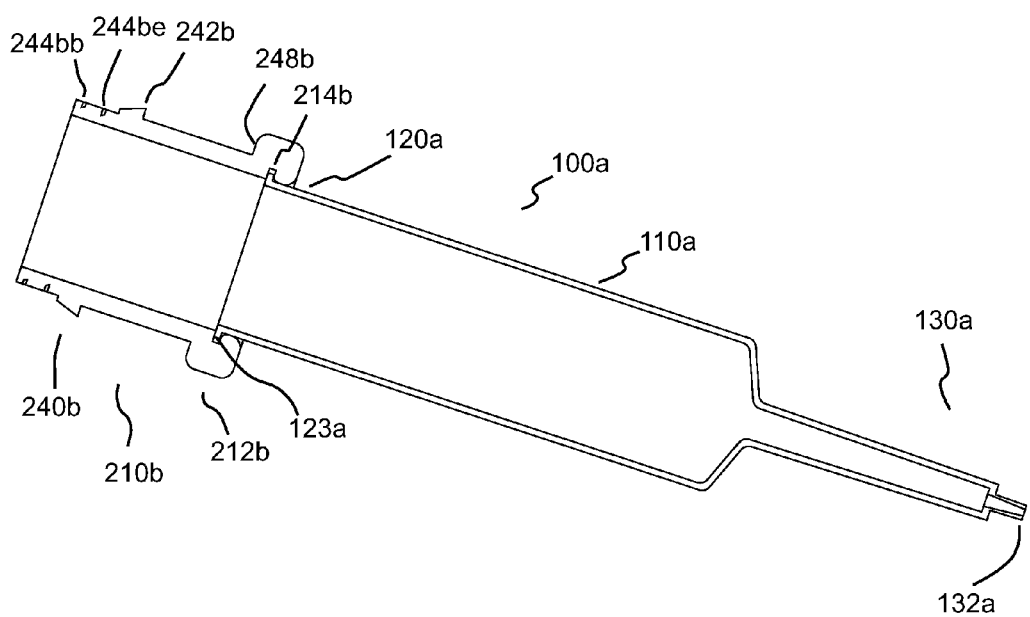
FIG. 4C illustrates a side cutaway view of the syringe adapter of FIG. 4A in operative connection with the syringe portion.

FIGS. 4A and 4B illustrate another embodiment of a syringe adapter 200b for use with the representative example of a 25 ml ULTRAJECT™ prefilled syringe 100a. In a number of respects, syringe adapter 200b operates in a similar manner to syringe adapter 200a, and several elements of syringe adapter 200b are referenced similarly to corresponding elements of syringe adapter 200a with the substitution of the designation "b" for the designation "a". In the embodiment of FIGS. 4A and 4B, syringe adapter 200b is divided longitudinally into two generally identical sections or halves 210b. Sections 210b includes a forward portion 212b that interacts with syringe flange 123a to connect syringe 100a thereto and a rearward portion 240b to operatively connect adapter 200b to syringe interface 20. Each section 210b has formed therein a seating 214b to seat a portion (that is, half of) syringe flange 123a. During assembly, one of sections 210b can be placed in operative connection with syringe 100a (that is, with flange 123a seated in seating 214b). The other of sections 210b can then be brought into operative connection with syringe 100a. Sections 210b can then be bonded together via sonic welding, solvent welding, snap fits, adhesion etc. as known in the polymer bonding and connecting arts.

As described above in connection with syringe adapters 200 and 200a, mounting flange 242b corresponds to and operates in a similar manner to mounting flange 122. Indicators 244bb and 244be correspond to and operate in a similar manner to indicators 124a and 124c of syringe 100, and cooperate with sensing assembly 50 to identify and indicate the configuration of the adapter 200b/syringe 100a assembly to injector control system 80. Further, projecting tab 246b corresponds to and operates in a similar manner to projecting tab 128 of syringe 100 to enable release of adapter 200b from operative connection with syringe interface 20. A radially outward extending ledge 248b at a rearward end of first portion 212b corresponds to and operates in a similar manner to flange 140 of syringe 100.

In several embodiments, the first section and the second section of the syringe adapters of the present invention can be brought together to be attached at a nonzero angle relative to a longitudinal axis of the barrel section of the syringe portion. For example, in the case of syringe adapters 200 and 200b, the first section and the second section of the syringe adapters are brought together to be attached and engage a syringe portion at an angle generally perpendicular to the longitudinal axis of the barrel section of the syringe portion. Connecting the sections of the syringe adapters of the present invention at an angle to the axis of the syringe barrel results in forces during and injection procedure (as a result of forward motion of the injector drive member and connected syringe plunger) that are distributed about the circumference of the adapter and/or misaligned with direction of connection of the sections of the syringe adapter, reducing the potential of disconnection (for example, via failure of a snap connection or an adhered seam).

The foregoing description and accompanying drawings set forth the preferred embodiments of the invention at the present time. Various modifications, additions and alternative designs will, of course, become apparent to those skilled in the art in light of the foregoing teachings without departing from the scope of the invention. The scope of the invention is indicated by the following claims rather than by the foregoing description. All changes and variations that fall within the meaning and range of equivalency of the claims are to be embraced within their scope.

What is claimed is:

1. A syringe assembly for connecting a syringe to an injector, the syringe assembly comprising:
 a first section defining an open slot;
 a detached second section shaped to slide into and seat within the open slot;
 a seating having a front abutment and a rear abutment, the seating formed on the first section, the first section comprising a rearward portion configured to operably connect the syringe assembly to an injector syringe interface, the rearward portion further comprising indicators arranged to cooperate with a sensing system and positioned at predetermined positions to reflect light; and
 snap connectors for joining the first section and the second section, wherein the seating is configured to receive and seat at least a portion of a flange of the syringe between the front abutment and the rear abutment.

2. The syringe assembly of claim 1, wherein the snap connectors comprise mechanical connectors for joining the first section and the second section.

3. The syringe assembly of claim 1, wherein the assembly attaches to the syringe at a nonzero angle relative to a longitudinal axis of a barrel of the syringe.

4. The syringe assembly of claim 1, wherein the assembly attaches to the syringe at an angle generally perpendicular to a longitudinal axis of a barrel of the syringe.

5. The syringe assembly of claim 1, wherein the first section and the second section are formed from a polymeric material.

6. The syringe assembly of claim 1, wherein the open seating receives the flange such that the syringe cannot rotate relative to the assembly.

7. The syringe assembly of claim 1, further comprising a passage formed when the first section and second section are engaged, the passage being capable of operatively connecting to a barrel of the syringe and allowing a drive member to pass through the passage and operably contact to a plunger slidably positionable within the barrel.

8. The syringe assembly of claim 1, wherein the rearward portion comprises a mounting flange.

9. The syringe assembly of claim 1, wherein the rearward portion comprises a projecting tab to enable release of the assembly from the injector syringe interface.

10. The syringe assembly of claim 1, wherein the rearward portion comprises a radially extending ledge.

11. The syringe assembly of claim 1, wherein the indicators indicate the configuration of the syringe to the injector.

12. The syringe assembly of claim 1, wherein the indicators correspond to a binary code.

13. The syringe assembly of claim 1, wherein the syringe assembly is formed of a polymeric material which is optically translucent.

14. The syringe assembly of claim 1, further comprising a plunger adaptor.

15. The syringe assembly of claim 1, wherein removal of the first section from the second section results in breakage.

16. The syringe assembly of claim 1, wherein removal of the first section and the second section from the syringe results in breakage.

17. The syringe assembly of claim 1, wherein the second section comprises at least one lateral extending section adapted to slide into and seat within the open slot.

18. A method of forming a syringe assembly comprising:
providing a syringe having a barrel, a front end outlet in fluid connection with the barrel, and a rear end flange;
providing an adapter comprising at least a first section defining an open slot, a detached second section shaped to slide into and seat within the open slot, and a seating having a front abutment and a rear abutment, the seating formed on the first section, the first section engageable with the second section by snap connectors for joining the first section and the second section, the first section further comprising a rearward portion configured to operably connect the syringe assembly to an injector syringe interface, the rearward portion further comprising indicators arranged to cooperate with a sensing system and positioned at predetermined positions to reflect light;
seating the rear end flange of the syringe in the seating; and
sliding the second section into the open slot in the first section to form an engagement between the at least first section and the second section thereby connecting the adapter to the syringe,
wherein the rear end flange of the syringe is seated between the front abutment and the rear abutment of the seating.

19. The method of claim 18, wherein removal of the first section and the second section from the syringe results in breakage.

20. The method of claim 18, wherein the indicators indicate the configuration of the syringe to the injector.

21. The method of claim 18, wherein the indicators correspond to a binary code.

22. The method of claim 18, wherein the syringe assembly is formed of a polymeric material which is optically translucent.

23. The method of claim 18, wherein the second section comprises at least one lateral extending section adapted to slide into and seat within the open slot.

24. A kit to enable a syringe to be operably connected to an injector, the kit comprising:
an adapter comprising at least a first section defining an open slot, a detached second section shaped to slide into and seat within the open slot, and a seating having a front abutment and a rear abutment, the seating formed on the first section, the first section being engageable with the second section, the first section comprising a rearward portion configured to operably connect the adapter to an injector syringe interface, the rearward portion further comprising indicators arranged to cooperate with a sensing system and positioned at predetermined positions to reflect light; and
snap connectors for joining the first section and the second section,
wherein the seating is configured to receive and seat at least a portion of a flange of the syringe between the front abutment and the rear abutment.

25. The kit of claim 24, wherein removal of the first section from the second section results in breakage.

26. The kit of claim 24, wherein removal of the first section and the second section from the syringe results in breakage.

27. The kit of claim 24, further comprising a plunger adaptor.

28. The kit of claim 24, wherein the indicators indicate the configuration of the syringe to the injector.

29. The kit of claim 24, wherein the indicators correspond to a binary code.

30. The kit of claim 24, wherein the adapter is formed of a polymeric material which is optically translucent.

31. The kit of claim 24, wherein the second section comprises at least one lateral extending section adapted to slide into and seat within the open slot.

* * * * *

UNITED STATES PATENT AND TRADEMARK OFFICE
CERTIFICATE OF CORRECTION

PATENT NO. : 9,242,040 B2  
APPLICATION NO. : 12/766411  
DATED : January 26, 2016  
INVENTOR(S) : Liscio et al.

Page 1 of 1

It is certified that error appears in the above-identified patent and that said Letters Patent is hereby corrected as shown below:

Title Page (75), under "Inventors", in Column 1, Line 3, delete "Michael McNeill," and insert -- Michael McNeil, --, therefor.

IN THE SPECIFICATION:
In Column 5, Line 7, delete "an front" and insert -- a front --, therefor.
In Column 5, Line 11, delete "illustrated" and insert -- illustrates --, therefor.
In Column 5, Line 39, delete "side," and insert -- side --, therefor.
In Column 8, Line 27, delete "piston 50" and insert -- piston 60 --, therefor.
In Column 9, Line 29, delete "second section 210" and insert -- first section 210 --, therefor.
In Column 13, Line 2, delete "and or" and insert -- and/or --, therefor.
In Column 15, Line 39, delete "cylindrical member 270a'" and insert -- cylindrical member 272a' --, therefor.
In Column 15, Line 42, delete "First member 270a'" and insert -- First cylindrical member 272a' --, therefor.

Signed and Sealed this  
Twenty-sixth Day of April, 2016

Michelle K. Lee  
*Director of the United States Patent and Trademark Office*